United States Patent
DiBenedetto et al.

(10) Patent No.: US 7,113,898 B2
(45) Date of Patent: Sep. 26, 2006

(54) METHOD FOR MODELING SIGNAL TRANSDUCTION IN CELLS

(75) Inventors: Emmanuele DiBenedetto, Nashville, TN (US); Daniele Andreucci, Florence (IT); Paolo Bisegna, Rome (IT)

(73) Assignee: Vanderbilt University, Nashville, TN (US)

(*) Notice: Subject to any disclaimer, the term of this patent is extended or adjusted under 35 U.S.C. 154(b) by 520 days.

(21) Appl. No.: 10/289,880

(22) Filed: Nov. 7, 2002

(65) Prior Publication Data

US 2003/0130828 A1 Jul. 10, 2003

Related U.S. Application Data

(60) Provisional application No. 60/338,222, filed on Nov. 8, 2001.

(51) Int. Cl.
*G06F 17/50* (2006.01)
*G06G 7/60* (2006.01)

(52) U.S. Cl. .............................. 703/2; 703/11; 702/19
(58) Field of Classification Search .................. 703/2, 703/11, 12; 435/7.2, 23; 702/19; 382/128
See application file for complete search history.

(56) References Cited

U.S. PATENT DOCUMENTS

| | | | |
|---|---|---|---|
| 5,488,589 A | 1/1996 | DeAngelis | 367/131 |
| 5,605,809 A * | 2/1997 | Komoriya et al. | 435/23 |
| 5,655,028 A * | 8/1997 | Soll et al. | 382/133 |
| 5,930,154 A | 7/1999 | Thalhammer-Reyero | 364/578 |
| 5,947,899 A | 9/1999 | Winslow et al. | 600/410 |
| 5,980,096 A | 11/1999 | Thalhammer-Reyero | 364/578 |
| 5,989,835 A * | 11/1999 | Dunlay et al. | 435/7.2 |
| 6,103,479 A * | 8/2000 | Taylor | 435/7.2 |
| 6,139,574 A | 10/2000 | Vacanti et al. | 623/1.44 |
| 6,165,225 A | 12/2000 | Antanavich et al. | 623/23.72 |
| 6,708,141 B1 * | 3/2004 | Schaff et al. | 703/2 |
| 2003/0018457 A1 * | 1/2003 | Lett et al. | 703/11 |

* cited by examiner

*Primary Examiner*—Thai Phan
(74) *Attorney, Agent, or Firm*—Jenkins, Wilson, Taylor & Hunt, P.A.

(57) ABSTRACT

The present invention provides a model that can be use to describe biological processes having a complex spatial geometry, for example, cell signaling processes. The models can also be used to model the pathology underlying diseases characterized by disrupted signaling pathways, and to identify target proteins at an appropriate site in a signal transduction network such that modulation of the target proteins elicits therapeutic effects. Methods of modeling diffusion processes, as well as machine-readable products embodying the methods are also disclosed.

31 Claims, 4 Drawing Sheets

METHOD FOR MODELING SIGNAL TRANSDUCTION IN CELLS

CROSS-REFERENCE TO RELATED APPLICATIONS

The present patent application is based on and claims priority to U.S. Provisional Application Ser. No. 60/338,222, entitled "METHOD FOR MODELING SIGNAL TRANSDUCTION IN CELLS", which was filed Nov. 8, 2001 and is incorporated herein by reference.

TECHNICAL FIELD

The present invention relates to a mathematical model of a biological process having a complex spatial geometry. The methods of the present invention can be employed to model many biological processes, such as cell signaling in general and vision in particular. The present invention also relates to understanding and modeling disease conditions, such as those involving a signal transduction network.

| Abbreviations and Symbols | |
|---|---|
| BIOS | basic input/output system |
| RAM | random access memory |
| ROM | read only memory |
| USB | universal serial bus |
| LAN | local area network |
| WAN | wide area network |
| SAN | system area network |
| cGMP | cyclic guanosine monophosphate |
| PDE | phosphodiesterase |
| PDE* | activated phosphodiesterase |
| $D_R$ | disc of radius R in a rod outer segment |
| H | height of a rod outer segment shell |
| R | radius of a disc |
| Rh | rhodopsin |
| G | G-protein |
| R* | activated rhodopsin |
| J | current |
| $\hat{\Omega}_\epsilon$ | cylindrical domain of a rod outer segment |
| $C_i$ | disc in a rod outer segment |
| $\epsilon$ | ratio of relative length scales between micro-and macroscopic scales |
| L | lateral boundary |
| $\delta$ | volume fraction of Ci with respect to $\Omega_0$ |
| $C_{io}$ | disc that is struck by a photon |
| $\kappa_{cGMP}$ | diffusivity coefficient for cGMP |
| $\kappa_{Ca}$ | diffusivity coefficient for Ca |
| $N_{AV}$ | Avagadro's number |
| GTP | guanosine triphosphate |
| GCAP | guanylate cyclase-activating protein |
| $K_{cat}$ | catalytic turnover rate |
| $K_M$ | Michaelis constant |
| $D_{R*}$ | diffusion coefficient of activated rhodopsin |
| $D_{G*}$ | diffusion coefficient of activated G-protein |
| $D_{PDE}$ | diffusion coefficient for PDE |
| $v_{RG}$ | rate at which R* activates G-protein molecules |
| $C_{PDE}$ | surface density of activatable PDE |
| $\tau_{PDE*}$ | mean lifetime of activated PDE |
| $\tau R*$ | mean lifetime of activated rhodopsin |
| G* | activated transducin |
| $\Sigma_{rod}$ | surface area of the boundary of the rod |
| $K_{ex}$ | half-maximal constant |
| $\mathscr{F}$ | Faraday constant |
| $f_{Ca}J$ | flux of the current J carried by $Ca^{2+}$ |
| $\Omega_{0,\epsilon}$ | interdiscal space |
| $S_\epsilon$ | width of cylindrical shell surrounding the discs in the rod outer segment |
| $\Sigma_\epsilon$ | layer of thickness $\epsilon$ |
| $\Omega_0$ | space of a cylinder |

BACKGROUND

Cells respond to their environment by processes known as signal transduction. A signal transduction process generally begins with a hormone, pheromone or neurotransmitter binding to its receptor, which in turn activates a cascade of biochemical events culminating in a cellular response. In a biological system (e.g., a cell), there can be many different types of cascades and each one of these cascades can be considered to be a signaling module which, when activated, leads to a cellular response. Cells have many different kinds of receptors and are faced with many different kinds of signals, and multiple modules can be activated and/or active at the same time. Often, these modules interact with each other such that the net cellular response is an integrative function of all the inputs (e.g., cascades) interacting with the cell's unique machinery, which can lead to a range of cell-specific responses. The complexity of signal transduction networks poses a challenge to traditional experimental analysis. Mathematical models that can help to explore and critically evaluate data are needed to deal with this biological complexity (Weng et al., (1999) *Science* 284: 92–96 and Bhalla et al., (1999) *Science* 283: 381–387).

The quantitative analysis of the behavior of enzymes using Michaelis-Menten kinetics assumes that the enzymes are in an aqueous three-dimensional space. However cells are not well-stirred sacs, and to quantitatively analyze cellular regulatory pathways it can be important to take into consideration the local concentration and time-dependent diffusion of second messengers and protein cascades (e.g., spatio-temporal effects).

To develop a more refined quantitative approach to this problem, partial differential equations are more adequate than ordinary differential equations. Biochemical components can be described in a point-to-point way, with a time-dependent evolution for description of signaling processes, metabolic processes, transport processes, and other biological processes.

Pointwise descriptions of the various components of signaling present a higher order of complexity with respect to global, average, and bulk descriptions in several regards. One aspect of the complexity is the difficulty in solving partial differential equations, either theoretically or numerically. Another aspect of the complexity is that pointwise descriptions naturally involve the geometry of the space in which these processes are analyzed.

In implementing partial differential equations that provide spatial and temporal resolution of the pathway, the highly complex geometry of a cell can be addressed mathematically. Some of the features that are implemented in the present invention include a novel mathematical treatment of the complex geometry of the cells via homogenization and concentrated capacity, as well as the coupled diffusion of second messengers with explicit spatial and temporal control using partial differential equations.

SUMMARY OF THE INVENTION

A method of modeling a signal transduction pathway in a cell is disclosed. Preferably the cell is from a vertebrate, more preferably a warm-blooded vertebrate. In a preferred embodiment, the method comprises determining a simulated geometry of a signaling pathway in a cell; and calculating spatial and temporal diffusion of a chemical species via the simulated geometry of the signal transduction pathway in the cell, whereby signal transduction in the cell is modeled. Optionally, the cell is a rod cell of a vertebrate eye.

A method of modeling a signal transduction pathway in a cell can also be carried out for a plurality of cells. Modeling of signal transduction in a tissue is thus accomplished.

A virtual cell model and a virtual tissue model produced by the methods of the present invention are also disclosed. For example, the virtual tissue model can be a retina model.

A computer program product comprising computer executable instructions embodied in a computer readable medium for performing steps for modeling a signal transduction pathway in a cell is also disclosed. The steps comprise determining a simulated geometry of a signaling pathway in a cell; and calculating spatial and temporal diffusion of a chemical species via the simulated geometry of the signal transduction pathway in the cell, whereby signal transduction in the cell is modeled. Optionally, the cell is a rod cell of a vertebrate eye. Optionally, the computer program product is employed for modeling signal transduction in a plurality of cells.

Preferably, the simulated geometry is determined via a homogenization approach, a concentrated capacity approach, or a combination thereof.

Preferably, the diffusion processes are "coupled" diffusion processes. Thus, in a preferred embodiment, the methods and models of the present invention are employed in any finite number of coupled second messenger-like processes involved in signal transduction. Also, the methods and models of the present invention can be employed for other diffusion processes, such as rhodopsin, G-protein, which are not technically second messengers. Also, the methods and models of the present invention are not limited to visual transduction but include any signaling pathway where several coupled diffusion processes take place.

Accordingly, it is an object of the present invention to provide a novel method of modeling a biological process, such as signal transduction. This and other objects are achieved in whole or in part by the present invention.

An object of the invention having been stated hereinabove, other objects will be evident as the description proceeds, when taken in connection with the accompanying Laboratory Examples and Drawings as best described hereinbelow.

DETAILED DESCRIPTION OF THE INVENTION

Figure 1:
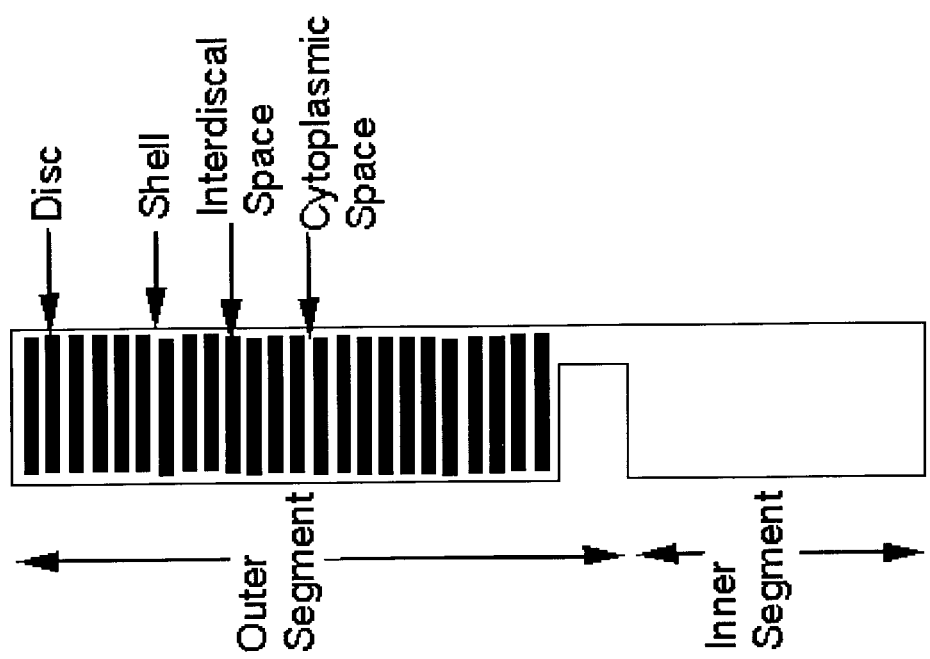
FIG. 1 is a schematic diagram of a rod cell.

I. Modeling Methods and Devices
I.A. A Method of Modeling a Signal Transduction Pathway in a Cell In one embodiment of the present invention, a method of modeling a signal transduction pathway in a cell is disclosed. In this embodiment, the method comprises first determining a simulated geometry of a signaling pathway in a cell. The simulated geometry, as well as the particular process for determining the simulated geometry, can be dependent on the nature of the signal transduction pathway and, consequently, on the nature of the cell in which the pathway is disposed. For example, the simulated geometry of a vision-related signal transduction pathway can be premised on the architecture of a rod cell, and more particularly on the outer segment of a rod cell.

In a method of the present invention, various signaling pathways can be described by a simulated geometry. For example, the methods are not limited to signal transduction, but can also be employed to model metabolic pathways and enzyme behavior.

A simulated geometry can be determined by examining the in vivo relationships of the components of a system. For example, in the case of vision transduction, the biological components of a rod outer segment (e.g., discs, outer shell of the rod, cytosol, interdiscal space, etc.) can be considered in determining a simulated geometry. A simulated geometry can account for the interrelation of the component parts of a system.

Although precise mathematical definitions of such structures can be formulated, often times it will be desirable to reduce these structures to simpler and more manageable descriptions. For example, a rod cell outer segment comprises a stack of approximately disc-shaped structures surrounded by an approximately cylindrical shell. Thus, a simulated geometry can be formulated that treats these sometimes-irregular biological components as simple, discrete geometric forms, such as discs and cylinders (see FIGS. 1 and 2). In another example, cone cells have a discrete geometry and can be conveniently treated by employing, as the name implies, a conical geometric model. Cone cells also comprise thin discs, and these discs can be modeled as the discs of a rod cell are modeled, for example as described herein.

Thus, in one aspect of the present invention, a simplified geometry can be employed to make the mathematical description of the system more manageable. In the context of vision transduction processes, this approach provides results that are in agreement with known theories and data, as indicated by numerical simulations. However, the methods of the present invention comprise a higher level model than those known in the art, since the methods of the present invention employ a spatio-temporal evolution approach. Methods known in the art do not account for spatio-temporal evolution and thus cannot adequately identify or describe various aspects of the process. For example, numerical simulations of the methods of the present invention have identified spatial phenomena, such as the progressive spread of activation along the outer shell of the rod, starting from the initial activation site.

Several aspects of the present invention involve employing homogenization theory and/or a concentrated capacity in the formation of a simulated geometry. The basis and mathematical treatment of these approaches in the context of the present invention is disclosed herein. Generally, a homogenized limit can be employed to simplify the formulation of a simulated geometry. Prior to the present disclosure, this approach has not previously been employed in a description of an in vivo signal transduction pathway.

When a homogenized limit is employed in a model of the present invention, the potentially overwhelming number of microscale descriptions required to fully describe the system (e.g., modeling of each microscale event) is significantly reduced. In the present invention, however, an insignificant degree of detail is lost when the microscale description is translated to a macroscale description. Thus, a simulated geometry can employ a homogenized limit to make numerical computations easier, or in some cases, possible.

In another aspect of a simulated geometry, processes can be described in terms of partial differential equations, instead of ordinary differential equations. A model employing partial differential equations frees the model from the assumptions that must typically be employed when ordinary differential equations are employed. Additionally, from an enzymology standpoint, the dependence of the model on Michaelis-Menten kinetics can be optionally eliminated.

A model can also incorporate a concentrated capacity. This approach, in effect, centralizes a diffusion process relative to a given location. Typically, this approach is applied in systems in which diffusion processes are occurring on thin, but three-dimensional, surface-like domains, for example the thin discs of a rod cell of the vertebrate eye. A concentrated capacity for these diffusion processes can be calculated by describing these processes in terms of evolution partial differential equations.

In a vision transduction model embodiment of the present invention, for example, diffusion can be concentrated on a surface, such as a rod outer shell. Such a concentration can be based on, for example, the geometry of the system or on principles of energy conservation. Due to the nature of biological systems, a capacity concentration of an in vivo process will most commonly incorporate energy conservation principles rather than geometric considerations, although some systems can be concentrated by employing both approaches.

In another aspect, a simulated geometry can account for coupled diffusion phenomena. For example, in the vision transduction pathway, $Ca^{2+}$ and cGMP concentration are coupled in the cytoplasm via the activity of guanylate cyclase, which is stimulated by the light induced lowering of calcium, and thus increases the concentration of cGMP and decreases the concentration of GTP. Such coupled diffusion phenomena are common in cell signaling processes and can be incorporated into a simulated geometry.

Continuing, spatial and temporal diffusion of a chemical species can then be calculated via the simulated geometry of the signal transduction pathway in the cell. Having determined a simulated geometry of the signal transduction pathway, numerical values can be inputted into the dimensionless model (some representative numerical values for a salamander rod cell are provided herein) and concentrations of one or more species can be calculated at a given point in time. Numerical simulations comprising a model of the present invention can also identify and/or describe various aspects of the system, such as the spread of activation along the outer shell of the rod from the activation site.

I.B. Method of Modeling the Diffusion of Two or More Entities in a Medium

In another embodiment of the present invention, a method of modeling the diffusion of two or more entities in a medium is disclosed. In this embodiment, the method comprises mathematically describing a medium. A medium can be any environment in which the entities, the diffusion of which is to be modeled, are disposed. Thus, a medium can be, for example, a cell or a tissue. Alternatively, a medium can also comprise a non-living system. In fact, although the embodiments described in the present disclosure are presented in the context of vision transduction and in vivo diffusion processes, the invention is not limited to such systems and the methods and models of the present invention can also be employed in non-living systems.

A mathematical description of the medium can be formulated by following the general approaches described herein. More specifically, the medium can be described in terms of geometrically-discrete forms. For example, a rod outer segment can be treated as a cylinder, while a cone outer segment can be treated as a conical form. The discs disposed in the rod and cone outer segments can be treated as thin discs or surfaces.

Next, boundary source terms for two or more entities can be determined. These boundary source terms can represent the boundary values of the two or more entities. The determination of these boundary source terms can be dependent on the interaction of the entities with themselves or with other components of the system. For example, due to the cascade effect in the outer segment of a rod cell, the concentration of PDE at a given point in time is dependent on the concentration of cGMP at that point in time, which is itself dependent on calcium ion concentration (see FIG. 3). Thus, in determining a boundary source term, the interrelation of various components of the system can be embodied in the boundary source term.

The method also comprises expressing the diffusion of at least one of the two or more entities as a homogenized limit. The advantages of describing the system as a homogenized system are described herein. Taking the rod outer segment as a model, a homogenized limit can be formed by mathematically increasing the number of discs in the rod outer segment while decreasing the distance between the discs as well as their thickness, such that the ratio of the volume of the discs to the volume of the cylinder remains constant. Effectively, this averages the diffusion processes in a given direction, for example the axial direction, when the discs are stacked face-to-face. The nature of the homogenized limit can depend on the geometry of the system.

Alternatively or in addition, the diffusion of at least one of the two or more entities onto a surface can be expressed as a concentrated capacity limit. In the context of a vision transduction model, diffusion occurring on the outer shell of the rod can be concentrated into a surface evolution equation on the outer boundary of the rod. Thus, by expressing diffusion of at least one entity as a capacity limit, which can be achieved as described herein, complex diffusion processes can be treated in the context of a simpler geometry. The reduction in complexity does not necessarily result in a reduction in accuracy or applicability of a model, however. To the contrary, the noted geometrical simplification forms an element of higher level models, since such models take into account spatio-temporal evolutions, a feature not found in known models.

In a model of the present invention, two or more diffusion processes can be linked. For example, in a vision transduction model, these two diffusion processes, namely diffusion in the cytosol, which is described by a homogenized limit, and diffusion on the rod outer shell, which is described as a concentrated capacity can be linked. Continuing with this example, these two diffusion processes can be linked by expressing the diffusing components in common terms. Conceptually, the processes are linked through the flux or through-flow of these diffusion processes. Thus, the disclosed mathematical descriptions of surface-to-volume reactions transcend classical enzyme dynamics, which deals exclusively with volume-to-volume processes.

Next, a spatial and temporal diffusion of one or more of the two or more entities by evaluating the homogenization limit and the surface evolution equation is calculated. After performing the previous steps of the method, this calculation can be performed by inputting measured or known values for the variables in the diffusion equations. Representative values for a salamander system are disclosed herein. By numerically calculating the spatial and temporal diffusion of various chemical species in a system, it is possible to not only to determine these values, but also to validate observed data. Indeed, numerical simulations of the models of the present invention indicate agreement with theory and known results. These simulations also indicate additional aspects of some diffusion processes, such as progressive activation along the surface of the outer shell of the rod.

I.C. A Program Storage Device

In yet another embodiment, a program storage device readable by a machine, tangibly embodying a program of instructions executable by the machine to perform method steps for modeling a signal transduction pathway in a cell is disclosed. The steps embodied in the program of instructions include determining a simulated geometry of a signaling pathway in a cell; and calculating spatial and temporal diffusion of a chemical species via the simulated geometry of the signal transduction pathway in the cell, whereby a signal transduction pathway in the cell is modeled. Particular aspects of these steps are described further herein.

Any form of program storage device can be employed in this and other embodiments of the present invention. Non-limiting examples of program storage devices include computer discs, CDs, hard drives and removable media.

Figure 4:
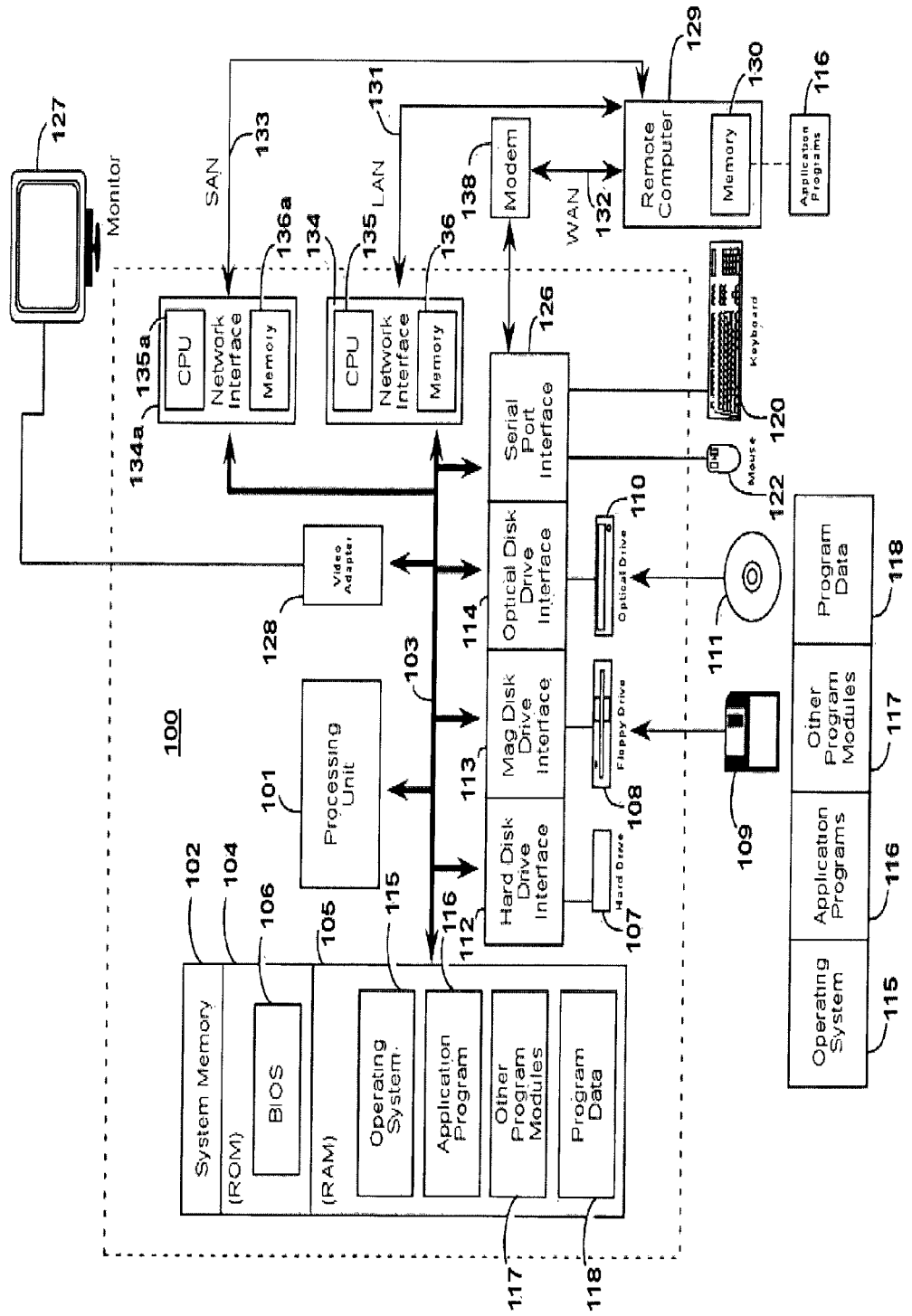
FIG. 4 illustrates an exemplary general purpose computing platform 100 upon which the methods and devices of the present invention can be implemented.

As noted, the methods and program storage devices of the present invention can be performed on a computer. With reference to FIG. 4, an exemplary system for implementing the invention includes a general purpose computing device in the form of a conventional personal computer 100, including a processing unit 101, a system memory 102, and a system bus 103 that couples various system components including the system memory to the processing unit 101. System bus 103 can be any of several types of bus structures including a memory bus or memory controller, a peripheral bus, and a local bus using any of a variety of bus architectures. The system memory includes read only memory (ROM) 104 and random access memory (RAM) 105. A basic input/output system (BIOS) 106, containing the basic routines that help to transfer information between elements within personal computer 100, such as during start-up, is stored in ROM 104. Personal computer 100 further includes a hard disk drive 107 for reading from and writing to a hard disk (not shown), a magnetic disk drive 108 for reading from or writing to a removable magnetic disk 109, and an optical disk drive 110 for reading from or writing to a removable optical disk 111 such as a CD ROM or other optical media.

Hard disk drive 107, magnetic disk drive 108, and optical disk drive 110 are connected to system bus 103 by a hard disk drive interface 112, a magnetic disk drive interface 113, and an optical disk drive interface 114, respectively. The drives and their associated computer-readable media provide nonvolatile storage of computer readable instructions, data structures, program modules and other data for personal computer 100. Although the exemplary environment described herein employs a hard disk, a removable magnetic disk 109, and a removable optical disk 111, it will be appreciated by those skilled in the art that other types of computer readable media which can store data that is accessible by a computer, such as magnetic cassettes, flash memory cards, digital video disks, Bernoulli cartridges, random access memories, read only memories, and the like may also be used in the exemplary operating environment.

A number of program modules can be stored on the hard disk, magnetic disk 109, optical disk 111, ROM 104 or RAM 105, including an operating system 115, one or more applications programs 116, other program modules 117, and program data 118.

A user can enter commands and information into personal computer 100 through input devices such as a keyboard 120 and a pointing device 122. Other input devices (not shown) can include a microphone, touch panel, joystick, game pad, satellite dish, scanner, or the like. These and other input devices are often connected to processing unit 101 through a serial port interface 126 that is coupled to the system bus, but can be connected by other interfaces, such as a parallel port, game port or a universal serial bus (USB). A monitor 127 or other type of display device is also connected to system bus 103 via an interface, such as a video adapter 128. In addition to the monitor, personal computers typically include other peripheral output devices, not shown, such as speakers and printers. With regard to the present invention, the user can use one of the input devices to input data indicating the user's preference between alternatives presented to the user via monitor 127.

Personal computer 100 can operate in a networked environment using logical connections to one or more remote computers, such as a remote computer 129. Remote computer 129 can be another personal computer, a server, a router, a network PC, a peer device or other common network node, and typically includes many or all of the elements described above relative to personal computer 100, although only a memory storage device 130 has been illustrated in FIG. 4. The logical connections depicted in FIG. 4 include a local area network (LAN) 131, a wide area network (WAN) 132, and a system area network (SAN) 133. Local- and wide-area networking environments are commonplace in offices, enterprise-wide computer networks, intranets and the Internet.

System area networking environments are used to interconnect nodes within a distributed computing system, such as a cluster. For example, in the illustrated embodiment, personal computer 100 can comprise a first node in a cluster and remote computer 129 can comprise a second node in the cluster. In such an environment, it is preferable that personal computer 100 and remote computer 129 be under a common administrative domain. Thus, although computer 129 is labeled "remote", computer 129 can be in close physical proximity to personal computer 100.

When used in a LAN or SAN networking environment, personal computer 100 is connected to local network 131 or system network 133 through network interface adapters 134 and 134a. Network interface adapters 134 and 134a can include processing units 135 and 135a and one or more memory units 136 and 136a.

When used in a WAN networking environment, personal computer 100 typically includes a modem 138 or other device for establishing communications over WAN 132. Modem 138, which can be internal or external, is connected to system bus 103 via serial port interface 126. In a networked environment, program modules depicted relative to personal computer 100, or portions thereof, can be stored in the remote memory storage device. It will be appreciated that the network connections shown are exemplary and other approaches to establishing a communications link between the computers can be used.

II. General Considerations

The largest class of signaling receptors is G protein-coupled receptors. G protein mediated cascades ultimately lead to the highly refined regulation of sensory perception, neuronal activity, cell growth and hormonal regulation. One of the best-studied eukaryotic signal transduction pathway is visual transduction (Liebman et al., (1987) *Ann. Rev. Physiol.* 49: 765–791 and Burns et al., (2001) *Ann. Rev. Neurosci.* 24: 779–805). In this system, the receiving cell is the photoreceptor, the signal is light, its receptor is rhodopsin, and the cellular response is a change in voltage at the photoreceptor's plasma membrane, which changes the cell's electrical output and leads to a signal being sent to the brain (Baylor, (1996) *Proc. Nat. Acad. Sci. USA* 93: 560–565).

Rod photoreceptors are composed of disk membranes containing high concentrations of the photoreceptor rhodopsin, the rod G protein, transducin or Gt, and the effector enzyme, cGMP phosphodiesterase (PDE) (Hamm, in *Cellular and Molecular Neurobiology*, (Saavedra, ed.) 11: 563–578 (1991)). Light activation of rhodopsin leads to activation of PDE, breakdown of cGMP, and closure of cGMP-sensitive channels in the plasma membrane, which hyperpolarizes the cell (Liebman et al., (1987) *Ann. Rev. Physiol.* 49: 765–791). Recovery from light excitation takes place through the decrease of [$Ca^{2+}$], the activation of guanylyl cyclase, and resynthesis of cGMP (Hurley, (1994) *Curr. Opin. Neurobiol.* 4: 481–487). This experimentally tractable signaling system has provided important insights into basic mechanisms of G protein-coupled signal transduction (Hargrave et al., *FASEB J.* 6(6): 2323–2331). Its input, light, can be presented in a precisely controlled way, and the output, the cell's voltage, is easily measured. The underlying protein components have been purified and recombined, and studied in vitro (Liebman et al., (1987) *Ann. Rev. Physiol.* 49: 765–791), and some of their three-dimensional structures have been solved (Palczewski et al., (2000) *Science* 289: 739–745 and Noel et al., (1993) *Nature* 366: 654–663). The cell's response to light is graded, based on light intensity, and is highly nonlinear.

Depending on the amount of light present, several different adaptation mechanisms are evoked (Detwiler et al., (1996) *Curr. Opin Neurobiol.* 6(4): 440–444 and Bownds et al., (1995) *Behavioral Brain Sci.* 18: 415–424). There is a great need to incorporate the data into a mathematical model. However, currently available models do not address the spatial complexity of the linked diffusion of cGMP and [$Ca^{2+}$] (Pugh & Lamb, (1993) *Biochem. Biophysica. Acta* 1141: 111–149; Pugh et al., *Curr. Opin. Neurobiol.* 9: 410–480; and Detwiler et al., (2000) *Biophys. J.* 79(6): 2801–2817).

In a representative embodiment of the present invention, the diffusion of cGMP in the cytosol of a rod cell, by a suitable homogenized limit, can be given the form of a family of diffusion equations holding on the geometric disc, parametrized with the axial variable as it ranges along the axis of a rod cell. The diffusion process taking place in the thin outer shell of the rod cell can be concentrated into a surface evolution equation on the outer boundary.

In the present invention, an explicit mathematical model of the temporal and spatial behavior of a signal transduction pathway leading to a cellular response is thus disclosed. In one aspect of the present invention, the mathematical model can be implemented in a computer program, which can be used as a versatile simulation tool, namely a virtual signal transduction model. Thus the predicted output of the mathematical model can be compared with known biological data.

Thus, in one aspect, the present invention provides a method of modeling a signal transduction pathway in a cell of a vertebrate. One method, for example, involves determining a simulated geometry of a signaling pathway in a cell via a simulation algorithm; and calculating spatial and temporal diffusion of a second messenger chemical species via an algorithm that employs the simulated geometry of the signal transduction pathway in the cell. Also provided are a computer program for performing the modeling methods and virtual cells produced by the method.

The model, modeling method and computer program product holds for cold-blooded (e.g. amphibians, for example salamanders, reptiles and fish) and warm-blooded vertebrates (mammals, preferably humans, and birds). The simulated geometry is generated using novel theoretical mathematical methods and thus can be generated by any kind of quantitative and theoretical methodology, including the use of formulas, equations, algorithms and like, as described further herein below.

There are many situations in which the methods of the present invention can be employed. For example, the methods can be employed to describe a signal transduction process occurring in a cell. Additionally, the methods can be employed to verify proposed signal transduction pathways or to identify observed failures in a signal transduction pathway. Such failures can be manifested in disease conditions. Thus, the models can also be used to model the pathology underlying diseases characterized by disrupted signaling pathways, and to identify target proteins at an appropriate site in a signal transduction network such that modulation of the target proteins elicits therapeutic effects. Other applications of the methods of the present invention will be apparent to those of ordinary skill in the art upon consideration of the present disclosure.

III. Model of Signal Transduction

In one aspect, the present invention discloses a mathematical model of signal transduction in a cell. This problem is complex and prior to the present invention, had not been adequately solved, due in part to the geometry of the domain occupied by the cytosol of a cell, and in part to fact that a cellular system typically comprises interactions between the several components in a cascade.

In the context of vision transduction, researchers in the art have recognized the importance of diffusion of the second messenger in the cytosol and its space-time dependence (see, e.g., Leskov et al., (2000) *Neuron* 27:525–537). Some have generated a mathematical model for the radial diffusion within a single interdiscal space (see, e.g., Dumke et al., (1994) *J. Gen. Physiol.* 103: 1071–1098). In these models, the longitudinal component of the diffusion is neglected. Others have taken into account only the diffusion along the axis of the rod, but neglect the space variables in the interdiscal space (see, e.g., Gray-Keller et al., (1999) *J. Physiol.* 519: 679–692). In both cases, a description of the mechanism by which interdiscal and outer shell diffusions interact is not addressed. Thus, these models do not take into account spatio-temporal evolutions.

Continuing with the treatment of visual transduction in the art, the diffusion coefficients of the rhodopsin, activated G-Protein and PDE are typically denoted by $D_{R*}$, $D_{G*}$ and $D_{PDE}$. Set $D=D_{R*}+D_{G*}+D_{PDE}$ ($D_{R*}=0.7$ µm$2^{s-1}$, $D_{G*}=1.5$ µm$\ $s$^{-1}$ and $D_{PDE}=0.8$ µm$^2$s$^{-1}$; Lamb & PughH, (1992) *J. Physiol.* 449: 719–758). Set also (noting $x_0=(x_{1,0}, x_{2,0})$ is the location on the lower face of the disc $C_{i_o}$ where the photon hits. In Lamb & Pugh, $x_0=0$), $$G^*(x, t) = \frac{v_{RG}}{4\pi D} E_1\left(\frac{|x-x_0|^2}{4Dt}\right) \text{ where } E_1(z) = \int_z^\infty \frac{e^{-s}}{s} ds \quad (1)$$

where $v_{RG}$ is the rate at which R* activates molecules of G-proteins ($v_{RG}$=7000 s$^{-1}$, Lamb & Pugh, (1992) *J. Physiol.* 449: 719–758). Then the space-time dependence of [PDE*] suggested by Lamb & Pugh, at least for early time points, is of the form, $$[PDE^*](x,t)=\min\{C_{PDE}; \frac{1}{2}G^*(x,t)\}, \quad (2)$$

where $C_{PDE}$ is the surface density of activatable PDE ($C_{PDE}$=167 μm$^{-2}$, Lamb & Pugh, (1992) *J. Physiol.* 449: 719–758. Full activation is assumed.). The main assumptions here are that R* and PDE are immobile, that the domain of diffusion is an infinite plane parallel to the disc $C_{i_0}$ and that diffusion of G* occurs with a diffusion coefficient as in Equation (2). The latter compensates for the stillness of R* and PDE. Note that this expression is valid during the activation phase (the time interval increase of PDE*).

Such an approach is not entirely satisfactory, as the functions in Equation (1), presumably derived from the explicit solutions of the heat equation (Fick's law) in an infinite plane, assume that the diffusion of rhodopsin, G protein and PDE can be lumped into a single diffusion process. Although the heat equation is linear, it is not linear in the diffusivity coefficients. The notion of compensating, while intuitively plausible, is not rigorous. Finally the semi-empirical nature of Equation (1) limits the modeling to the activation phase only.

Interpreting [PDE*](t) as the total number of molecules uniformly distributed in the rod, Nikonov et al. (Nikonov et al., (2000) *J. Gen. Physiol.* 116: 795–824), introduce the time-decay functional behavior, $$2[PDE^*](t) = \Phi v_{RP} \frac{\tau_{PDE^*} \tau_{R^*}}{\tau_{PDE^*} - \tau_{R^*}} \left\{ e^{\frac{-t}{\tau_{PDE^*}}} - e^{\frac{-t}{\tau_{R^*}}} \right\} \quad (3)$$

where $\Phi$ is the number of photoisomerizations, $v_{RP}$ is the rate at which R* activates molecules of PDE, the numbers $\tau_{PDE^*}$ and $\tau_{R^*}$ are the mean lifetimes of R* and PDE* respectively ($v_{RP}$=6300s−1, Lamb & Pugh, (1992) *J. Physiol.* 449: 719–758, $\tau_{PDE^*}$≈2s. and $\tau_{R^*}$=0.4s, Nikonov et al., (2000) *J. Gen. Physiol.* 116: 795–824). This reduces to a pointwise description of [PDE*], and returns to the notion of bulk quantities. While it exhibits a time-decay mechanism through proportionality constants, the precise form of such a decay is not demonstrated.

Another type of time-decay behavior is exhibited by Gray-Keller et al. (Gray-Keller et al., (1999) *J. Physiol.* 519: 679–692). The dependence upon the radial variables is neglected and the dependence on the axial variable is given of the form, $$[PDE^*](z, t) = \gamma t e^{-\frac{t}{\tau}} e^{-\frac{z^2}{L^2}}, \quad (4)$$

for a characteristic length L (L≈1 μm; Gray-Keller et al., (1999) 519: 679–692). Thus, the form of the rod is lumped into the segment (0, H) where the variable z ranges. These approaches all have in mind at least two features: (i) a space decay behavior, away from the activation site, accounting for the diffusion on the receptor, the transducin and the effector; and (ii) a time decay mechanism, accounting for recovery and/or inactivation of the receptor and of the effector. These features are reminiscent, even at an intuitive level of the explicit solution, of the heat equation in the whole space.

In contrast, a model of the present invention is based, in one aspect, on the evolution of partial differential equations set in the cytosol. This approach affords a precise description of the various components of the phenomenon at the actual location where they occur. For example, in one embodiment, a model for the diffusion of the second messengers cGMP and Ca$^{2+}$ within the cytosol, (i.e., the interdiscal spaces and the outer shell, of a rod cell of the vertebrate eye) is disclosed. As depicted in FIG. 1, in a rod cell the cytosol is disposed within the bounds of the rod outer shell. As shown schematically in FIGS. 1–3 activated PDE (PDE*)-cGMP interactions, which physically occur on the surface of the discs, are correctly modeled as flux sources located on the discs $C_i$. This addresses the interaction of an enzyme bound to a membrane with a substrate distributed in the cytoplasm. Similarly, the evolution of Ca$^{2+}$ is effected by influx through cGMP-gated channels and efflux through exchangers and this process is depicted in FIG. 3. This process is described by source terms supported on the lateral boundary of the rod. In the existing art, analogous source terms are treated as volume-averaged quantities, rather than in terms of their actual physical location.

Another feature of a model of the present invention is the local role played by the geometry of the domain occupied by the cytosol. The diffusion of the second messengers takes place in a domain that is thin along the axial direction (i.e., along the interdiscal space in the rod cell) and along the radial direction (i.e., along the outer shell in the rod cell). In terms of the model, this geometry suggests expressing diffusion effects taking place in such a complex geometry (schematically presented in FIG. 1) as diffusion processes. Homogenization theory (e.g., describing thin discs stacked up in a periodic way and involving several different scales) and concentrated capacity (e.g., describing a thin outer shell where the diffusion is to be concentrated and involving localized diffusion) are also employed in aspects of the present invention. Referring again to FIGS. 1 and 2, the diffusion of cGMP in the cytosol, by a suitable homogenized limit, can be given the form of a family of diffusion equations holding on the geometric disc $D_R$, parametrized with the axial variable z, as it ranges along the axis of the rod (i.e., z ∈ (0,H)). Likewise, the diffusion process taking place in the thin outer shell of the rod can be concentrated into a surface evolution equation (by the Laplace-Beltrami operator) on the outer boundary {|x|=R}x (0, H). Coordinates in $\mathbb{R}^2$ are denoted by x=($x_1$, $x_2$) and in $\mathbb{R}^3$ by (x, x)=($x_1$, $x_2$, z). The two diffusions communicate by sharing their flux (in a suitable sense) in such a way that the boundary diffusion is the trace of the "interior" diffusion.

The limiting system of partial differential equations, set in a simple geometry, facilitates the ability to perform more efficient numerical implementations. Thus, in one aspect of the present invention, such numerical implementations can be investigated numerically and their output can be compared with the existing experimental data. One such a comparison indicates that the numerical results of a model of the present invention agree with known experimental data. The numerical component of the present invention simulates both the full model and its homogenized limit, and can be employed to compare predictions and to validate the usefulness and computational efficiency of the latter as a substitute for a full model.

In another aspect of the present invention, a description of the concentration of chemical species in a signaling pathway is disclosed, e.g. activated PDE (PDE*), as a function of position (x) and time (t) in a visual transduction model. This aspect of the present invention, in itself, also represents an advance in the field. Due in part to the complexity of the system, a satisfactory full modeling of the function [chemical species, e.g. PDE*](x, t) has been a major open problem and is addressed by the present invention.

Figure 2:
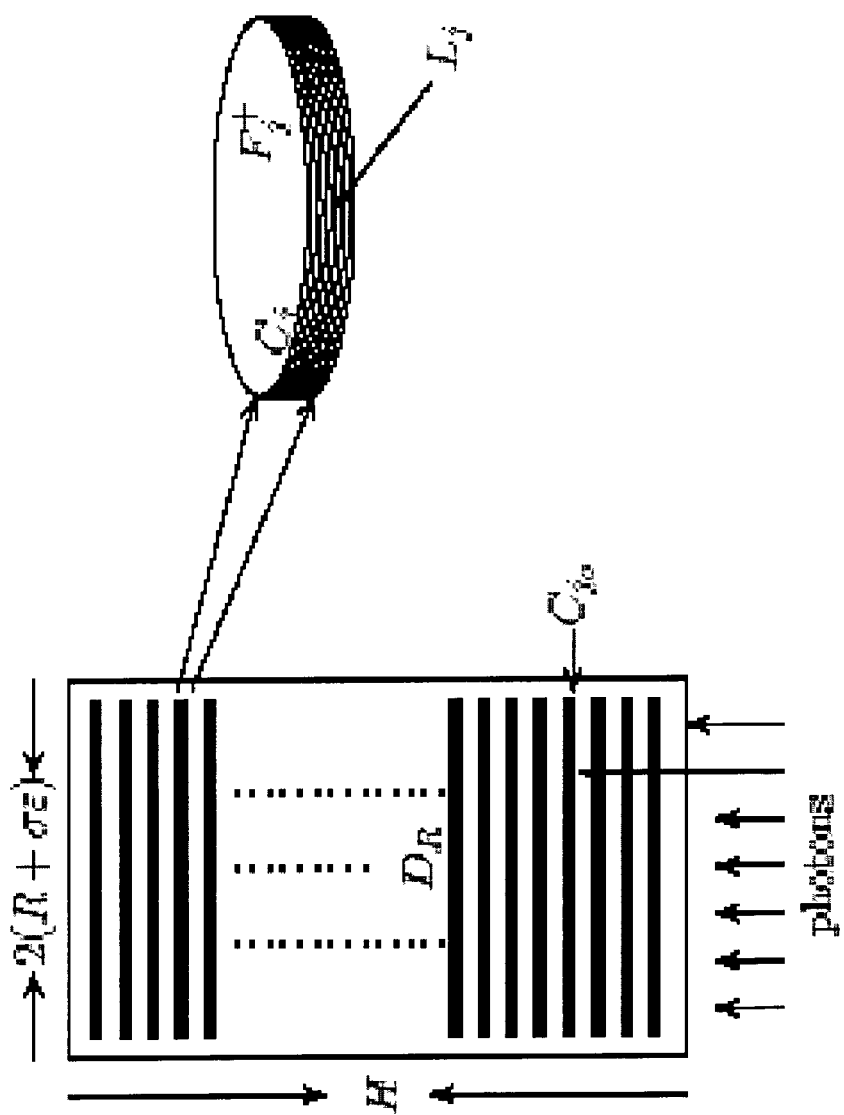
FIG. 2 is a simplified schematic diagram depicting the impact of photons on the discs of the discs of the outer segment of a rod cell.
Figure 3:
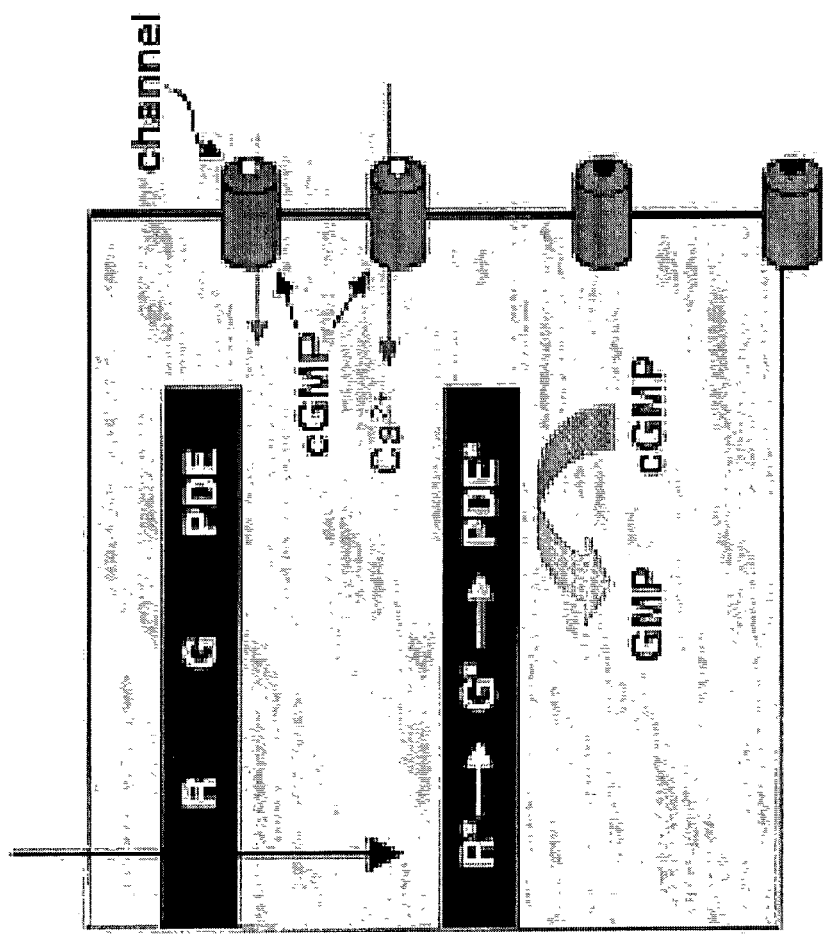
FIG. 3 is a schematic of processes that occur in the discs and those that occur in the cytoplasm in a rod cell. The figure depicts the activation of PDE on the discs and the formation of guanosine monophosphate (GMP) from cyclic guanosine monophosphate (cGMP) in the cytoplasm.

Continuing with FIGS. 1–3 in which PDE* is presented as an example, a model for the function [PDE*](x, t), exhibits, in one embodiment, at least the following features: (i) a space decay behavior, away from the activation site, which accounts for the diffusion of transducin, the receptor and an effector; and (ii) a time decay mechanism, accounting for recovery and/or inactivation of the receptor and of the effector.

IV. General Approach to the Model

The following sections describe representative, non-limiting general concepts that can be useful in a description of the theoretical aspects of the present invention. In one aspect, the present invention involves the use of homogenization theory to formulate a macroscopic scale description of a phenomenon (e.g., vision transduction) that accounts for microscopic diffusion events (e.g., second messenger diffusion), but is not limited by an unwieldy and unworkable description encompassing each microscopic diffusion event.

Broadly, homogenization theory deals with processes that are occurring on two scales in a heterogeneous medium, such as biological structures (e.g., tissue, organs, etc.). In such a medium, there are two or more length scales that need to be considered, namely a microscopic scale, and a macroscopic scale. The microscopic scale can address structures and processes occurring on a molecular scale (e.g., molecular dynamics), while the macroscopic scale can address the overall processes to which these microscopic scale processes contribute.

Often, the interest of mathematical modelers is focused on identifying and describing events that occur on the macroscopic scale, with less interest placed on events occurring on the microscopic scale, which can themselves give rise to a macroscopic scale process. This is due primarily to the fact that the solution of the equations describing the microscopic scale events is typically unattainable for any system other than the most simple systems. Often, this is because a complete description of the microscopic scale events is too large to practically generate, manage or use.

Thus, it is a goal of homogenization theory to generate macroscopic descriptions of events that take into account microscopic scale events, while still remaining solvable and not completely dominated by such events. This is commonly referred to as "upscaling" the descriptions of microscopic scale events to the more manageable and useful macroscopic scale. Homogenization theory accomplishes this goal by preparing equations describing the macroscopic event, while progressively extending the scale parameter to zero (i.e., to the microscopic scale). By preparing such a description, the focus on events occurring on the microscopic scale is minimized, leaving a solvable macroscopic description of a process that can be dependent, in part, on microscopic scale events.

In a model of the present invention, homogenization theory is employed to describe a simulated geometry of a signaling pathway in a cell. In a representative example, the diffusion of cGMP in the cytosol of the interior of a rod cell of the vertebrate eye is described. Attention is given to a description of the notation employed in the theoretical aspects of the present invention. As homogenization theory dictates, and as FIG. 1 suggests, there are several different scales involved in a model of the present invention, namely a macroscopic scale and a microscopic scale. This arrangement is particularly suited to treatment via homogenization theory. The macroscopic scale is denoted by the subscript $x_0$, while the microscopic scale is denoted by the subscript $x_1$. The scale parameter $\epsilon$ describes the relationship between the micro- and macroscopic scales. These different scales arise from the different diffusion rates that occur at different locations. In the example of a vision transduction model, diffusion rates are different for the outer surface of a rod outer segment, for the discs that make up the outer segment, and for the gaps that exist between the discs in the outer segment of a rod.

In another aspect of the present invention, a concentrated capacity is employed to describe a simulated geometry of a signaling pathway in a cell. In a model of vision transduction, this addresses diffusion processes taking place in the outer shell of the rod (i.e., on a surface), and diffusion processes within the cytosol (i.e., within a volume) are concentrated into a single surface evolution equation. Thus, by combining these two approaches in the vision transduction model, diffusions occurring in the outer shell of the rod and within the rod in the cytosol can be linked. Such related equations can then be linked to the electrical current arising from transport of electrolytes (e.g., $Na^+$ and $K^+$) through ion channels, which is subsequently passed to the brain and forms a basis of vision.

V. Biological Considerations

The methods of the present invention can be employed to describe a signal transduction pathway in any kind of cell. For example, the methods can be employed to describe signal transduction in a tumor cell. In another aspect, a model of the present invention can be employed to describe vision transduction and processes occurring in a rod cell. A discussion of a visual transduction model of the present invention follows, by way of illustration and not limitation. Before a mathematical treatment of this process is presented, a brief discussion of the fundamental biology of this system is presented.

Referring again to FIGS. 1–3, the outer segment of a rod photoreceptor is a right cylinder of height H and cross section a disc $D_{(1+\sigma\epsilon)R}$ of radius $(1+\sigma\epsilon)R$, for positive numbers $\sigma$, $\epsilon$ and R. A rod receptor has at least about three major functional regions: (i) the outer segment, located at the outer surface of the retina, contains the light-transducing apparatus; (ii) the inner segment, locate proximally within the retina, contains the cell's nucleus and most of its biosynthetic machinery; and (iii) the synaptic terminal, makes contact with the photoreceptor's target cells. The following discussion is primarily focused on the rod outer segment, which is the functional region of the rod receptor in which phototransduction reactions occur.

The cylinder houses a vertical stack of n equispaced parallel discs, each of radius R, width $\epsilon$ and mutually separated by a distance $\nu\epsilon$. Even though the discs have incisures (of varying width and depth according to species), in the first stage of the model, the incisures are assumed to be disc-like. The outer shell is the gap $S_\epsilon=(D_{(1+\sigma\epsilon)R}-D_R)\times(0, H)$. (For the salamander $H\approx 22$ µm, $n\approx 800$, $R\approx 5.5$ µm, $\epsilon\approx 14$ nm, $\nu\epsilon\approx 14$ nm, $\sigma\epsilon\approx 15$ nm; see Pugh & Lamb, (1993) *Biochim. Biophys. Acta* 1141: 111–149).

Each disc is made up of two functionally independent layers of lipidic membrane where proteins such as rhodopsin (Rh) (the light receptor), G-protein (G), also called transducin, and phosphodiesterase (PDE), also referred to as effectors, are embedded. These proteins can move on the face of the disc where they are located, but cannot abandon the disc. The lateral membrane of the rod contains uniformly distributed channels of small radius. In the dark these channels are open and are permeable to sodium (Na$^+$) and calcium (Ca$^{2+}$) ions. The space within the rod not occupied by the discs, is filled with fluid cytosol, in which cyclic-guanosine monophosphate (cGMP) and Ca$^{2+}$ diffuse.

Referring particularly to FIG. 3, assume a photon hits a molecule of rhodopsin, located on one of the discs, $C_{io}$. The rhodopsin becomes activated (denoted by R*), and in turn activates any G-protein it touches. Each of the activated G-proteins G* is capable of activating one and only one molecule of PDE on the disc $C_{io}$, by binding to it upon contact. The activated PDE is denoted by PDE*. This cascade takes place only on the disc $C_{io}$. The next cascade, involving cGMP and Ca$^{2+}$, takes place in the cytosol.

Active PDE* degrades cGMP thereby lowering its concentration. The decrease of concentration of the cGMP causes closure of some of the cGMP gated membrane channels, resulting in a lowering of the influx of Na$^+$ and Ca$^{2+}$ ions, and thus a lowering of the local current J across the outer membrane. The dependence of J on the concentration [cGMP] is given by a Hill-type law, $$J = \frac{\gamma [cGMP]^\kappa}{K_{cGMP}^\kappa + [cGMP]^\kappa} \quad (5)$$

where $\gamma$, $\kappa$ and $K_{cGMP}$ are positive parameters. The Na$^+$/Ca$^{2+}$/K$^+$ exchanger removes Ca$^{2+}$ from the cytosol and because it is no longer flowing in through the channels, a decrease in the calcium concentration is observed. This decrease in calcium, in turn, results in the disinhibition of guanylate cyclase and the synthesis of cGMP and a consequent reopening of the channels. The same decrease of calcium activates rhodopsin kinase, which phosphorylates rhodopsin. Phosphorylated rhodopsin binds arrestin and can no longer activate G protein. Thus PDE* decays to zero, ending the depletion of cGMP.

Summarily, in vertebrates, after rhodopsin undergoes a conformational change, it initiates a cascade which ultimately leads to a decrease in the concentration of cGMP. In the cell, when cGMP is associated with ion channels, the channels are open. When cGMP concentration in the cells drops, less cGMP associates with the ion channels and the channels close. When the ion channels close, ions (e.g., cations) do not enter the cell and, effects a hyperpolarization of the membrane, leading to transmission of an electrical impulse to the brain. Subsequently, cGMP concentration is restored, the ion channels reopen and the membrane repolarized.

VI. Geometry of the Rod Outer Segment of the Eye

The rod outer segment is identified with the cylindrical domain $\Omega_\epsilon = D_{(1+\sigma\epsilon)R} \times (0, H)$, where $D_{(1+\sigma\epsilon)R}$ is a disc of radius $(1+\sigma\epsilon)R$, centered at the origin of $\mathbb{R}^2$, and R, $\sigma$, $\epsilon$ and H are positive numbers.

The manifolds $C_i$, i=1, 2, . . . , n, carrying the rhodopsin are assumed to be a thin coaxial cylinders, of cross section a disc $D_R$, of radius R and height $\epsilon \ll H$. A schematic of this arrangement is depicted in FIGS. 1 and 2. The $C_i$ are equally spaced, i.e., the upper face of $C_i$ has distance $v\epsilon$ from the lower face of $C_{i+1}$, where $v$ is a positive number. The first $C_i$ has distance $\frac{1}{2}v\epsilon$ from the lower face of the rod $\tilde{\Omega}_\epsilon$ and the last $C_n$ has distance $\frac{1}{2}v\epsilon$ from the upper face of the rod. The upper and lower faces $F_i^\pm$: of the disc $C_i$ and its lateral boundary $L_i$ can be described by:

$$F_i^\pm = D_R \times \{z_i \pm \tfrac{1}{2}\epsilon\}; \ L_i = \{|x|=R\} \times (z_i - \tfrac{1}{2}\epsilon, z_i + \tfrac{1}{2}\epsilon) \text{ where}$$
$$z_i = (1 - \tfrac{1}{2}\epsilon)(1+v)\epsilon.$$

Each of the $C_i$ can be regarded as being cut out of the central cylinder $\Omega_0 = D_R \times (0, H)$ formally obtained from $\Omega_\epsilon$ be setting $\epsilon = 0$. The indicated geometry implies that the parameters $\epsilon$, $v$ and the number n of manifolds carrying the rhodopsin are linked by $$(n - 1/2)(1+v)\varepsilon = H - 1/2(1+v)\varepsilon \ i.e.,$$

$$n\varepsilon = \frac{H}{1+v}; \ \frac{n \cdot vol(C_{1,\varepsilon})}{vol(\Omega_0)} = \frac{1}{1+v} \stackrel{def}{=} \delta.$$

The parameter $\delta$ is the volume fraction of the union of the disk $C_i$ with respect to rod $\Omega_0$. The homogenization limit can be carried out by letting $\epsilon \to 0$ and $n \to \infty$ and by keeping $\delta$ constant.

The second messengers, i.e., cGMP and calcium ions (Ca$^{2+}$), diffuse in the subset of $\tilde{\Omega}_\epsilon \subset \Omega_\epsilon$ not occupied by the cylinders $C_i$. Since within $\Omega_\epsilon$ there are no volume-sources for either cGMP and Ca$^{2+}$, $$\begin{aligned} \frac{\partial [cGMP]}{\partial t} - div_{\kappa_{cGMP}} \nabla [cGMP] &= 0 \\ \frac{\partial [Ca^{2+}]}{\partial t} - div_{\kappa_{Ca}} \nabla [Ca^{2+}] &= 0 \end{aligned} \quad \text{in } \tilde{\Omega}_\varepsilon = \Omega_\varepsilon - \bigcup_{i=1}^n C_i \quad (6)$$

where $\kappa_{cGMP}$ and $\kappa_{Ca}$ are the respective diffusivity coefficients in $\mu m^2 s^{-1}$. For the salamander, $\kappa_{cGMP} \approx 60 \ \mu m^2 s^{-1}$ in Koutalos et al., (1995) *Biophys. J.* 68: 373–382, and $\kappa_{Ca} \approx 5$–$10 \ \mu m^2 s^{-1}$ in Koutalos & Nakatani, (1999) *Biophys. J.* 76: A242.

VII. Boundary Source Terms

The following discussion can also be used as a guide in formulating a description of boundary source terms for other variables in models prepared as disclosed herein in the context of the exemplary but non-limiting vision transduction embodiment of the present invention. In the context of the vision transduction embodiment of the present invention, such boundary source terms describe limits on the concentrations of cGMP and Ca$^{2+}$.

VII.A. Boundary Source Terms for cGMP

An idealized experiment by which a small beam of photons, hits disc $C_{i0}$ (depicted in FIG. 2) on one of its faces (e.g. the lower face), at coordinate $z_0$ along the axis of the rod can be modeled. The beam $D_\eta(x_0, z_0)$ is considered as uniformly distributed within $D_\eta(x_0, z_0)$, centered at $(x_0, z_0)$ and having a radius $\eta > 0$ so small that the space occupied by the beam $D_\eta(x_0, z_0)$ is contained on the lower face of $C_{i0}$.

Boundary values of volumic quantities such as cGMP are interpreted by the standard mathematical notion of "traces" of functions in Sobolev spaces, on lower dimensional manifolds (Adams, *Sobolev Spaces*, Academic Press, New York, 1975; DiBenedetto, *Real Analysis*, Birkhäluser, Boston, 2000; Mazia, *Sobolev Spaces*, Springer-Verlag, New York, 1985).

Production or depletion of molecules of cGMP occurs through binding phenomena on the lower and upper face of each of the cylinders $C_i$. Precisely, cGMP is depleted as it binds to dark-activated phosphodiesterase (PDE), at a rate, $$\kappa[PDE][cGMP], k=\text{catalytic rate of dark-activated PDE.} \quad (7)$$

Here [PDE] is defined as the surface density of PDE, uniformly distributed on the total area of the faces of the discs $C_i$, i.e., $$[PDE] = \frac{\text{total number of } PDE \text{ molecules in the rod}}{2n\pi R^2 N_{AV}}, \quad (8)$$

where n is the number of the discs in the rod and $N_{AV}$ is Avogadro's number. $\kappa=4\times10-2$ $\mu M^{-1}s^{-1}$, Stryer, (1991) *J. Biol. Chem.* 266: 10711–10714. Since production or depletion of molecules of cGMP occurs on the faces of the cylinders $C_i$, "rates" are measured in number of μmol of the substrate, per unit surface and per unit time. It is assumed that there is no background light. (see Nikonov et al., (2000) *J. Gen. Physiol.* 116: 795–824) for I=0.

Also, cGMP is generated by the guanylate cyclase (GC) that is bound on the faces of cylinder $C_i$. Molecules of guanosine triphosphate (GTP) bind to molecules of guanylate cyclase to generate molecules of cGMP. Such activity is modulated by $Ca^{2+}$. $Ca^{2+}$ is bound to guanylate cyclase-activating protein (GCAP). As the concentration of $Ca^{2+}$ decreases GCAP is released and is free to bind to guanylate cyclase and to change its activity. Diffusion of GCAP is assumed to be negligible, so that molecules of GCAP are essentially still within $\tilde{\Omega}_\epsilon$. Thus, only those near the faces of the cylinders $C_i$ and in contact with the guanylate cyclase (GC) affect the process. The rate of conversion of GTP into cGMP as a function of $[Ca^{2+}]$ is given by an experimental Hill-type relation, (9) {rate of production of [cGMP] on the faces of the discs $C_i$}=

$$\frac{\kappa_{GC}[GC]}{1+9([Ca^{2+}]/\beta)^m}$$

where $\kappa_{GC}$ is the catalytic rate of guanylate cyclase and [GC] is the surface density of GC, uniformly distributed on the total area of the faces of the discs $C_i$, i.e., $$[GC] = \frac{\text{total number of GC molecules in the rod}}{2n\pi R^2 N_{AV}}$$

$$= \frac{\text{total number of GC molecules in the rod}}{n\pi v \varepsilon R^2 N_{AV}}$$

$$= \frac{v\varepsilon}{2} \frac{\text{total number of GC molecules in the rod}}{(\text{volume of interdiscal space}) \cdot N_{AV}}$$

The same rate of production of cGMP is given in Gray-Keller et al., (1999) *J. Physiol.* 519: 679–692, as a source term within the domain $\tilde{\Omega}_\epsilon$ available for the diffusion. As indicated, it is a boundary source to be prescribed as a component of the flux of cGMP on each of the faces of cylinders $C_i$.

$$\text{Setting } \alpha = k_{GC} \frac{\text{total number of GC molecules in the rod}}{(\text{volume of interdiscal space}) \cdot N_{AV}}$$

the rate in (9) takes the form:
(10) {rate of production of [cGMP] on the faces of the discs $C_i$}=

$$\frac{(1/2)v\varepsilon\alpha}{1+9([Ca^{2+}]/\beta)^m}$$

The constant ½vεα, is the maximum rate of production of cGMP, corresponding to absence of $Ca^{2+}$, and β is the $Ca^{2+}$ density that achieves ½ of the maximum rate. The positive number m is Hill's constant. For the salamander rod, α=13 μMs$^{-1}$, β=87 nM and m=2.1, in Koutalos & Yau, (1996) *Trends Neurosci.* 19: 73–81.

Let $C_{io}$ be the disc hit by the photon and let $(x, t) \to [PDE^*](x, t)$ be the resulting surface density of activated PDE. By the Michaelis-Menten relation (assuming full activation)

$$\left\{ \begin{array}{l} \text{rate of depletion of } [cGMP] \text{ on the} \\ \text{lower face of } C_{10}, \text{ due to } PDE^* \end{array} \right\} = K_{cat} \frac{[cGMP]}{K_M + ([Ca^{2+}]/\beta)^m} \quad (11)$$

where $K_{cat}$ is the catalytic turnover rate and is measured in s$^{-1}$, wherein $K_M$ is the Michaelis constant.

It is typical to neglect the contribution of [cGMP] in the denominator of the right hand side of Equation (10), in favor of $K_M$ (the maximum value of [cGMP] is approximately 4 μM, whereas $K_M \geq 40$ mM, Lamb & Pugh, (1992) *J. Physiol.* 449: 719–758), i.e., to set $$\left\{ \begin{array}{l} \text{rate of depletion of } [cGMP] \text{ on the} \\ \text{lower face of } C_{10}, \text{ due to } PDE^* \end{array} \right\} = k^*[cGMP][PDE^*], \quad (12)$$

where $k^*=K_{cat}/K_M$ is the catalytic rate of the light-activated PDE ($k^* \approx 60$ μM$-1^{s-1}$, i.e., $k^* \approx 1500$ k, Stryer, (1991) *J. Biol. Chem.* 266: 10711–10714. Koutalos & Yau, (1996) *Trends Neurosci.* 19: 73–81, suggest a dependence of $k^*$ on calcium). Combining these descriptions, the source terms on the faces $F_i^\pm$ of the discs take the form $$k_{cGMP} \frac{\partial [cGMP]}{\partial z}\bigg|_{F_i^\pm} = \pm k[PDE][cGMP] \mp \frac{(1/2)v\varepsilon\alpha}{1+([Ca^{2+}]/\beta)^m} - \quad (13)$$

$$\delta_{zo} k^*[PDE][cGMP],$$

where $\delta_{zo}$ is the Dirac mass on $\mathbb{R}$ concentrated at $z=z_0$. In Equation (13) the product k[PDE] is taken-to be constant, since dark-activated [PDE] diffuses considerably less than the corresponding light-activated [PDE*]. This is also justified by the relation $k^*=1500$ k. For the salamander rod, k[PDE]=1 s$^{-1}$ (Nikonov et al., (2000) *J. Gen. Physiol.* 116: 795–824) and Gray-Keller et al., (1999) *J. Physiol.* 519: 679–692, and k[PDE]=0.3 s$^{-1}$ (Koutalos & Yau, (1996) *Trends Neurosci.* 19: 73–81).

It is assumed that there are no source terms on the lateral part $L_i$ of the boundary of the cylinders $C_i$, as well as on the boundary of the rod $\partial\Omega_\epsilon$, i.e:

$$k_{cGMP} \nabla[cGMP] \cdot x|_{L_i} = 0 \text{ and } k_{cGMP} \nabla[cGMP] \cdot n_i|_{\partial\Omega_\epsilon} = 0 \quad (14)$$

VII.B. Boundary Source Terms for $Ca^{2+}$

Calcium does not penetrate the discs $Ci$ carrying the rhodopsin, so that $$kCa \nabla[Ca^{2+}] \cdot n_{i=0} \quad (15)$$

where $n_i$ is the unit inner normal to $C_i$. Ions of $Ca^{2+}$ are lost through the lateral boundary of the rod by electrogenic exchange and are gained by their influx, through the cGMP-activated channels.

The current density $J_{ex}$ across the boundary of the rod, due to electrogenic exchange is modeled by a Michaelis-Menten type relation, $$J_{ex} = \frac{j_{ex,sat}}{\sum_{rod}} \frac{[Ca^{2+}]}{[Ca^{2+}] + K_{ex}} \quad (16)$$

Here $\Sigma_{rod}$ is the surface area of the boundary of the rod, $j_{ex;sat}$ is the maximal or saturation current as $[Ca^{2+}] \to \infty$, and $K_{ex}$ is the half-maximal constant (for the salamander, $j_{ex;sat}=17$ pA and $K_{ex}=1500$ nM; Nikonov et al., (2000) *J. Gen. Physiol.* 116: 795–824. From above, $\Sigma_{rod}=(5/2)\pi 11^2 \mu m^2$). Therefore, $$\{\text{rate of change of } [Ca^{2+}] \text{ due to electrogenic exchange}\} = \quad (17)$$

$$-\frac{j_{max}}{\sum_{rod}} \frac{[cGMP]^k}{[cGMP]^k + K_{cGMP}^k}$$

for a positive constant $\Theta$ (Nikonov et al., (2000) *J. Gen. Physiol.* 116: 795–824), the contribution due to electrogenic exchange is volumetric, i.e., the current $j_{ex;sat}$ is divided by the volume of the cytosol. The constant $\Theta$ is then given of the form $\Theta=(a\mathscr{F})^{-1}$ m where $\mathscr{F}=96500$ C mol$^{-1}$ is the Faraday constant and a is some a-dimensional number that takes into account buffering effects within the cytosol. Since the electrogenic exchange takes place through the Na$^+$/K$^+$/Ca$^{2+}$ exchanger on the boundary of the rod, and it is local in nature, such a contribution here is taken as a boundary source.). The current density J, carried by the cGMP-activated channels, across the boundary of the rod, is given by the Hill's type law, $$J = \frac{j_{max}}{\sum_{rod}} \frac{[cGMP]^k}{[cGMP]^k + K_{cGMP}^k} \quad (18)$$

where $j_{max}$ is the maximal current as $[cGMP] \to \infty$ and $K_{cGMP}$ is the half-maximal constant (for the salamander, $K_{cGMP}=32$ $\mu$M and $\kappa=2$; Nikonov et al., (2000) *J. Gen. Physiol.* 116: 795–824. In formula A11 of Nikonov et al., $K_{cGMP}$ is given to be itself a function of $[Ca^{2+}]$, with range 13–32 $\mu$M of cGMP, as $[Ca^{2+}]$ ranges over $[0, \infty]$). Thus, $$\{\text{rate of production of } [Ca^{2+}] \text{ due to its influx through cGMP-activated channels}\} = \frac{1}{2}\Theta f_{Ca} J \quad (19)$$

where $\Theta$ is as in Equation (17) and $f_{Ca}$ is a non-dimensional number in $(0,1)$ (the product $f_{Ca}J$ is the portion of the flux of the current J, carried by $Ca^{2+}$. For the salamander, $f_{Ca}$ is 0.17; Nikonov et al., (2000) *J. Gen. Physiol.* 116: 795–824. These remarks give the flux of calcium across the boundary of the rod in the form, $$k_{Ca}\nabla[Ca^{2+}] \cdot n = \quad (20)$$

$$-\Theta \frac{j_{ex,sat}}{\sum_{rod}} \frac{[Ca^{2+}]}{[Ca^{2+}] + K_{ex}} + \frac{1}{2}\Theta f_{Ca} \frac{j_{max}}{\sum_{rod}} \frac{[cGMP]^k}{[cGMP]^k + K_{cGMP}^k}$$

VIII. Modeling [PDE*](x,t)

A form for [PDE*](x, t) could be concocted using portions of Equations (1)–(4) to reflect the various behaviors. Such an approach however would have to mediate between the different modeling assumptions involved in the derivation of Equations (1)–(4).

One approach of a vision transduction model of the present invention incorporates the observation that rhodopsin diffuses on the discs (but not between discs) and follows a diffusion equation. Specifically, rather than "guessing" or approximating the form of an equation(s) describing this phenomenon, a vision transduction model of the present invention employs mathematics to identify this description as a solution of another Fick's-type diffusion on the disc hit by a photon. Similarly, the forms of the G protein and PDE are the result of their own diffusion processes on the discs. The forcing terms of these forms can be devised from the Law of Mass Action (i.e., R=k[A]x[B]y, where R is the rate of a reaction, [A]x is the molar concentration in A, [B]y is the molar concentration in B and k is a rate constant), thus reducing the modeling to a first-principle approach.

Continuing with the description of [PDE*](x,t), rhodopsin diffuses on the disc $C_{io}$ where light-activation occurs. The initial data for such a diffusion phenomenon is a Dirac mass concentrated at the point $X_o \in C_{io}$, where the photon acts. The rhodopsin in turn serves as a source term into a diffusion process affecting only the activated transducin (G*). The initial data and the boundary variational data for the G* are zero. The output of G* binds to the PDE, producing PDE*. The latter satisfies, in turn, a Fick's law. The various source terms can be derived by repeated application of the Law of Mass Action.

IX. A Dimensionless Model

The modeling approaches disclosed herein generate naturally a factor of n−1 in the source terms of Equations (8), (10), (12). This reflects in the factor $\epsilon$ in the dimensionless source Equation (22) below. This feature provides a natural framework for the homogenized limit.

In one aspect of the preparation of a dimensionless model, namely the formation of a homogenized limit, lengths are rescaled by $\mu$m and renamed as R, H, $D_R$, $\Omega_0$, $\Omega_{68}$, the corresponding, non-dimensional configurational elements of the rod. Also [cGMP] and [Ca$^{2+}$] are rescaled by $\mu$M, time is rescaled by s, and the conductivities are rescaled by $\mu$Ms$^{-1}$. Then, set, $$u_\varepsilon = \frac{[cGMP]}{\mu M}, \, v_\varepsilon = \frac{[Ca^{2+}]}{\mu M}, \, k_u = k_{[cGMP]} \frac{s}{\mu m^2}, \, kv = k[Ca^{2+}] \frac{s}{\mu m^2}$$

where the index $\epsilon$ refers to the domain $\tilde{\Omega}_\epsilon$, where the functions $u_\epsilon$ and $u_\epsilon$ are defined. By these rescalings, Equation (6) takes the dimensionless form, $$u_{\epsilon,t} - k_u \Delta u_\epsilon = 0, \ v_{\epsilon,t} - k_v \Delta v_\epsilon = 0 \ \text{in} \ \tilde{\Omega}_\epsilon. \tag{21}$$

Similar rescaling on the boundary conditions Equation (21) yields, in dimensionless form, $$k_u u_{\epsilon x}|_{F_i^\pm} = \pm \gamma_0 \epsilon u_\epsilon \mp \nu \epsilon f_1(v_\epsilon) - \delta_{zo} u_\epsilon f_2(v_\epsilon; x, t), \ i=1, 2, \ldots, n \tag{22}$$

where $\gamma_0$ is a given positive constant, $f_j$ are positive, smooth bounded functions of their arguments. The specific form of $f_2(v_\epsilon; x, t)$ depends on the modeling of $[PDE^*](x, t)$ as indicated herein above (note that $f_2$ might depend on $v_\epsilon$ through $k^*$). The form of $f_1$ is derived from Equation (10), i.e., $$f_1(s) = \frac{\gamma_1}{\beta_1^m + s^m} \text{for given positive constants } \gamma_1, \beta_1. \tag{23}$$

Analogously, the boundary conditions Equations (14) and (15) take the dimensionless form:

$$k_u \nabla u_\epsilon \cdot x|_{L_i} = 0 \text{ and } k_v \nabla v_\epsilon \cdot n_i = 0, \ I = 1, 2, \ldots, n. \tag{24}$$

Finally, boundary sources in Equation (20) become $$k_u \nabla v_\epsilon \cdot n = -g_1(v_\epsilon) + g_2(u_\epsilon) \tag{25}$$

where $s \to g_j(s)$ are positive, smooth, bounded functions of their argument. Moreover, $g_j(0) = 0$ and $g_j(s) \to \lambda_j$ as $s \to \infty$ for two positive constants, $\lambda_j$. Specifically, $$g_1(s) = \frac{c_1 s}{d_1 + s} \text{ and } g_2(s) = \tag{26}$$

$$\frac{c_2 s^\kappa}{d_2^\kappa + s^\kappa} \text{ for given positive constants } c_j, d_j \text{ and } \kappa.$$

IX.A. The Homogenized Limit

The geometry of a rod exhibits two thin compartments available to the diffusion of the second messengers $Ca^{2+}$ and cGMP. Precisely, the interdiscal space $\Omega_{0,\epsilon}$ between the internal stack of discs, and the outer shell $S_\epsilon$, i.e. the thin cylindrical shell surrounding the discs. With the symbolism employed herein, $$\Omega_{0,\epsilon} = \{D_R \times (0, H)\} - \bigcup_{i=1}^n \overline{C_i}; \ S_\epsilon = \{D_{(1+\sigma\epsilon)R} - D_R\} \times (0, H). \tag{27}$$

The boundary of the interdiscal space contributes with the reaction terms in Equation (22)–(26), whereas the diffusion is prevalent in the radial directions. The numerical values for c (i.e., the constants) as well as a consideration of available electron micrographs of the rod outer segment, indicates that c<<R, i.e., the thickness of the interdiscal spaces is negligible with respect to the radius R. For this reason some in the art have indicated that the radial diffusion within the interdiscal spaces is not essential. On the other hand, such a diffusion cannot be neglected as it is the only physical space from which cGMP can flow to the activated PDE on the disc where the photon falls. Also c<<H, i.e., the thickness of $S_\epsilon$ is negligible with respect to its height H. However, despite the small width of $S_\epsilon$ the axial diffusion within $S_\epsilon$ might play a role, since it is the only portion of the cytosol connecting the interdiscal spaces. Tangential diffusion in $S_\epsilon$ also plays a role if the process is not radially symmetric (this situation might occur, for example, if the incoming photon does not fall at the center of the disc $C_{io}$). The thin region $S_\epsilon$ is also essential in modeling the exchange of $Ca^{2+}$ between the cytosol and the extracellular space.

Regarding $\epsilon$ as a parameter, allowing $\epsilon \to 0$ allows one to recover, in the limit, a problem set in a simpler geometry but that preserves the some, if not all, of the physical features of interest of the original geometry. Generally, it is possible to increase the number of discs and reduce accordingly their mutual distance and their thickness, in such a way that the ratio, $$\delta = \text{total volume of discs/volume of } \Omega_o = \frac{1}{1+\nu} \text{ remains constant.}$$

Broadly, as $\epsilon \to 0$, the diffusing process is averaged in the axial direction. Results indicate that the functions $\{u_\epsilon\}$ and $\{v_\epsilon\}$, representing dimensionless cGMP and $Ca^{2+}$ concentrations within each $\tilde{\Omega}_\epsilon$ and satisfying Equation (21), tend in a sense to be made precise, to functions u and v, satisfying $$u_t - k_u \Delta_{(x_1, x_2)} u = F(u, v) + \delta_{zo} G(u, v); \tag{28}$$

$$v_t - k_v \Delta_{(x_1, x_2)} v = 0; \text{ in } \Omega_o; \left( \Delta_{(x_1, x_2)} = \frac{\partial^2}{\partial x_1^2} + \frac{\partial^2}{\partial x_2^2} \right).$$

The boundary reaction terms originating from Equation (22) appear in the limit as the volumetric source terms F(u,v) and G(u,v) distributed in $\Omega_0$. Thus the 3-dimensional diffusion ($\Delta_{(x1,x2,z)}$) expressed in Equation (21) and set in the layered domain $\tilde{\Omega}_\epsilon$ is reduced to a 2-dimensional diffusion ($\Delta_{(x1,x2)}$) set in the right cylinder $\Omega_0$, which has a simple geometry. In the mathematical theory of diffusion, such an averaging process is known as forming a homogenized limit. The notion of limit, the appropriate topologies, and in what sense Equation (28) are satisfied, are preferably made precise.

IX.B. The Limit of Concentrated Capacity

In Equation (28) the diffusion operator involves only the variables $(x_1, x_2)$, i.e., broadly, the diffusion operator acts on a plane normal to the axis of the cylinder $\Omega_0$. However the functions u and v also depend on the axial variable $z \in (0, H)$, as they are affected by the diffusion process taking place on the outer shell $S_\epsilon$.

As $\epsilon \to 0$, the outer shell $S_\epsilon$, formally approaches the surface $S_o = \{|x| = R\} \times \{0, H\}$. To preserve the axial and tangential diffusion of cGMP and $Ca^{2+}$ on the shells $S_\epsilon$ the vanishing of the width of $S_\epsilon$ are preferably balanced by a suitable rescaling of the diffusivity in Equation (21). Such a rescaling, as $\epsilon \to 0$, is preferably performed so that, for each $\epsilon > 0$, the axial flux is preserved. Also, the flux exchange with the inner domain $\Omega_0$ and the outer environment is preferably preserved by a suitable description.

Continuing, denote by w the formal limit, on the surface $S_o$, of the functions $\{u\epsilon\}$ restricted to the outer shells $S\epsilon$. Results indicate that w satisfies $$w_t - k_o \Delta s_o w = \{\text{sources}\}, \text{ in } S_o, \tag{29}$$

where $\Delta s_o$ is the Laplace-Beltrami operator on $S_o$, the constant $k_0$ is a suitable limit of the rescaled diffusivities and the source terms are generated by the indicated balances of fluxes to be enforced for all $\epsilon>0$. Also, the trace of u on $S_o$ must equal w. Similar considerations hold for a limiting equation for the dimensionless $Ca^{2+}$ concentration.

Such a process, where diffusion in a thin but three-dimensional domain is constrained to a diffusion within a surface by a proper resealing of the diffusion coefficients, is known as limit of concentrated capacity.

The use of the homogenized limit and the limit of concentrated capacity, in the context of phototransduction, fits the geometry of FIG. 1. The use of a homogenized limit is also consistent with a treatment of the thermal properties of thin material regions, for example the bending of thin metal plates when subjected to loads.

IX.C. Homogenization of the Inner Cylinder

Homogenization of elliptic equations in periodically perforated domains is a tool in the investigation of the mechanical and thermal properties of composite materials (Bensoussan et al., *Asymptotic Analysis for Periodic Structures*, North-Holland Publishing, Amsterdam, Holland, 1978; Cioranescu & Paulin, *Homogenization of Reticulated Structures*, Springer-Verlag, New-York, 1999, *Applied Mathematical Sciences* Vol. 136; and Oleinik et al., *Mathematical Problems in Elasticity and Homogenization*, North-Holland Publishing, Amsterdam, Holland 1992). The process typically comprises two steps. First, one solves an elliptic partial differential equation in a domain $\Omega_\epsilon$ with many cavities distributed in some periodic way. Data (which is typically homogeneous) are then assigned on the boundary of the cavities. Let $\{u_\epsilon\}$ be the family of the corresponding solutions. One then studies the behavior of the family $\{u_{68}\}$ and the form of a "limiting" partial differential equation as the perforations become finer and finer. The problem lies in identifying such a limiting differential equation, its solutions, and their relation to the approximating family $\{u_\epsilon\}$.

The limiting equation is, in general, quite different from the approximating equations. This is so even if the limiting differential equation is formally the same as the one set in each $\Omega_\epsilon$.

The limit of the family $\{u_\epsilon\}$ also depends on, among other factors, the geometry of the cavities $G_\epsilon$ and the boundary conditions imposed on their boundaries. Additionally, the boundary source terms can appear, in the limit, as volumetric sources (Jäger et al., (1997) *Appl. Anal.* 65: 205–223 and Yosifian, (1997) *Appl. Anal.* 65: 257–288).

Considering the above in the context of the present invention, in the geometry of FIGS. 1 and 2, (which depict a schematic of an outer rod segment), the cavities are represented by the discs $C_i$. These are not periodic in the usual sense of homogenization theory (see, for example, Oleinik et al., *Mathematical Problems in Elasticity and Homogenization*, North-Holland Publishing, Amsterdam, Holland, 1992). These discs instead exhibit a structure vaguely resembling the tall thin frames studied in Cioranescu & Paulin, *Homogenization of Reticulated Structures*, Springer-Verlag, New-York, *Applied Mathematical Sciences* Vol. 136, 1999.

Unlike the treatments provided in the art (e.g., Cioranescu & Paulin, *Homogenization of Reticulated Structures*, Springer-Verlag, New-York, *Applied Mathematical Sciences* Vol. 136, 1999), however, the boundary source terms disclosed herein (i.e., Equation (22)) are not homogeneous and are not linear. In addition, some of the present boundary source terms, (for example, the one originating from the cylinder $C_{io}$) contribute like a "Dirac mass" concentrated at the level $z=z_0$. Non-homogeneous and linear boundary conditions appear in a geometry of a periodic array of cavities that comprise cubes (Jäger et al., (1997) *Appl. Anal.* 65: 205–223 and Oleinik & Shaposhnikova, (1995) *Rendiconti Lincei: Matematica e Applicazioni* 6: 133–142). In the present invention, however, the geometry of the cavities (i.e., the discs $C_i$) is fixed by the physical model itself, making the methods of present invention unlike approaches in the art.

IX.D. Concentrating the Capacity on the Outer Shell

In one aspect of a visual transduction model of the present invention, a concentrated capacity approach is employed to describe diffusion of species on the surface of the outer shell of a rod. Diffusion processes occurring in thin, three-dimensional, surface-like domains, can be evaluated by thinking of these thin three-dimensional domains as surfaces, denoting by $\Sigma_\epsilon$ a generic layer of thickness $\epsilon$, and by $\{u_\epsilon\}$ the solutions of evolution partial differential equations $(PDE)_\epsilon$ holding in $\Sigma_\epsilon$. Each $(PDE)_\epsilon$ is given precise boundary conditions, which might be variational, Dirichlet, and/or mixed. In practice, one lets $\epsilon \to 0$ to obtain formally a surface $\Sigma_0$, a "limiting" equation $(PDE)_0$ holding on $\Sigma_0$ and a solution $u_0$ for such a $(PDE)_0$.

For the limiting problem not to be vacuous, the boundary data associated with $(PDE)_\epsilon$ needs to be suitably rescaled in terms of the parameter $\epsilon$. One of the main challenges associated with this class of problems is that the resealing mechanism of the boundary data affects both the limiting equation and the limiting solutions, and therefore, there is no canonical way of identifying such a limit (Colli & Rodrigues, (1990) *Asymptotic Anal.* 3: 249–263; Erzhanov et al., *Concentrated Capacity in Problems of Thermophysics and Micro-Electronics*, Naukova Dumka, Kiev, 1992; and Savarè & Visintin, (1997) *Atti della Accademia nazionale dei Lincei. Classe di scienze fisiche, matematiche e naturali. Rendiconti lincei. Matematica e applicazioni* 8(1): 49–89). In practice, the method employed to rescale the boundary data is suggested by either the geometry of the system or by energy considerations (e.g., conservation of various combinations of mass and energy flux).

By way of example, consider the first of the equations of Equation (21) restricted to the outer shell $\Sigma_\epsilon$. To stress such a localization, one denotes by $w_\epsilon$ the restriction of $u_\epsilon$ to $\Sigma_\epsilon$. On the exterior part of the lateral boundary of $\Sigma_\epsilon$ the functions $w_\epsilon$ all have homogeneous Neumann conditions, since no cGMP diffuses beyond the bounds of the outer segment. On the interior part of the lateral boundary of $\Sigma_\epsilon$ the functions $w_\epsilon$ must all coincide with $u_\epsilon$, and their normal derivatives must coincide with the normal derivatives of $u_\epsilon$, i.e., $$w_\epsilon = u_\epsilon \alpha v \delta \Delta w_\epsilon \cdot \frac{x}{|x|} = \nabla u_\epsilon \cdot \frac{x}{|x|} \text{ on } |x| = R. \quad (30)$$

Thus Equation (21), when regarded independently, is given the overdetermined data of Equation (30) on the portion of the boundary $\{|x|=R\}$. This complication, which can be the main challenge of the problem, can also be its redeeming feature. Indeed the overdetermination of Equation (30) can restrict the number of possible rescaling mechanisms, thus eliminating the ambiguity of the limit of concentrated capacity.

X. Computer Implementation

Continuing with a vision transduction embodiment of the present invention, the spatial and temporal resolution (i.e., a spatio-temporal description) of the pathway depend, in part, on dealing with the highly complex geometry of the rod outer segment. This problem is addressed by employing homogenization and concentrated capacity approaches. Thus, the computational capabilities of the models of the present invention are at least twofold and include the ability to provide (1) a numerical simulation of the full, non-homogenized system; and (2) a numerical simulation of the "homogenized" and "concentrated" system. The models of the present invention can thus be employed to provide numerical solutions to questions posed regarding the concentration and/or behavior of a cascade member at a given point in time.

Although a non-homogenized model can be employed in a description of a biological or other phenomenon, a homogenized model of the present invention can provide results very similar to those achievable with a full non-homogenized model (e.g., a model that does not employ a homogenization approach). Additionally, the models of the present invention are highly valuable because they can drastically reduce the computations necessary to model the whole system, which can be numerous and render the full, non-homogenized model unworkable. Furthermore, a homogenized model can provide accurate and reliable numerical results without sacrificing the details embodied in the non-homogenized model.

The numerical challenges of a numerical simulation of the full, non-homogenized system stem from at least (a) the potentially complex geometry of the rod cell, which comprises hundreds of thin membranes (discs) on which non-linear boundary conditions, which require rather fine grids in both the radial and axial directions, are imposed; (b) disparate spatial scales, since rod cell diameters areas 3 orders of magnitude greater than interdiscal distances; and (c) low diffusivities. These factors can lead to relatively slow diffusion, requiring many time steps and thus, long and complex computations.

Preferably the computations associated with identifying numerical solutions are carried out by high performance computing systems (a representative system is disclosed in FIG. 4). This can be achieved, for example, via parallelization for distributed-memory clusters of processors and/or heterogeneous networked computers. Since there is no functional parallelism in solving partial differential equations, it is possible to employ natural data parallelism, via domain decomposition, to solve certain equations. This can be achieved by assigning groups of discs to different processors, which can pass their boundary values to their neighbors at each time step.

Referring again to the visual transductor embodiment, the system of partial differential equations can be discretized in space by finite volumes (e.g., integrated finite differences), on a circular cylinder representing the photoreceptor segment of a retinal rod cell (i.e., the rod outer segment), and by higher order explicit schemes. Some reasons for the latter choice are that small time-steps are sometimes desired for accuracy, and that super-time-stepping acceleration can be employed (Alexiades et al., (1996) *Commun. Numer. Meth. En.* 12: 31–42) to significantly speed up execution of the explicit scheme. Additionally, parallelizing an explicit scheme is easier to implement and more efficient to run.

Thus, in one aspect of the present invention, a computer implementation of a mathematical model of signal transduction is disclosed. In one embodiment, the computer implementation of the model can be developed hand-in-hand with the mathematics. In forward mode, the computer model can be employed to conduct computational experiments for interpretation of available biological data, compare model predictions with measurements, make determinations of sensitivity of output on various model parameters, and to design further biological experiments. In reverse mode, it can be employed to determine physical parameter values that are difficult, infeasible, or substantially impossible to measure directly.

Thus, a mathematical model of the present invention provides in part: for: (1) modeling the behavior of membrane bound enzymes and channels which determine the temporal and spatial evolution of second messengers; (2) a freedom from assumptions based on bulk Michaelis-Menten kinetics; (3) via homogenization, the number and extent of computations needed to simulate such complex cellular behaviors as the cell's responses to signals in its environment are drastically reduced; and (4) a freedom from the many simplifying assumptions required by earlier models based on ordinary differential equations.

In its computer-implemented form, the model is user friendly, and can be modified as desired to develop it into a modular tool that can be broadly useful to cell biologists who want to study the quantitative aspects of various biophysical phenomena, including signal transduction, metabolic pathways or enzyme behavior in cells.

XI. Employing and Extending a Model of the Present Invention

To demonstrate the accuracy and utility of a mathematical model of the present invention, the model can be employed on actual literature data from the sizable body of data already available. For example, the measures of the electrical output of rod photoreceptors can be tested under a variety of light regimes, including the single photon response (Baylor et al., (1979) *J. Physiol.* 288: 613–634; Rieke & Baylor, (1998) *Biophysical J.* 75: 1836–1857) responses to flashes of a large range of intensities, responses to flashes during steady light input (Lamb et al., (1981) *J. Physiol.* 319: 463–496; Matthews et al., (1988) *Nature* 334: 67–69; Nakatani & Yau, (1988) *J. Physiol.* 395: 695–729; Lagnado et al., (1992) *J. Physiol.* 455: 111–142), and dark adaptation (Lamb, (1980) *Nature* 287: 349–351). In addition, data from "knock-out" animals missing one component of the cascade at a time can be fitted to a model of the present invention (Chen et al., (2000) *Nature* 403: 557–560; Chen et al., (1999) *Proc. Natl. Acad. Sci. USA* 96: 3718–3722; and Chen et al., (1995) *Science* 267: 374–377). Thus, the present invention facilitates a complete and explicit description of most, if not all, steps in the visual transduction and adaptation process, and can be employed to describe additional systems as well.

Having identified a precise formalism for the diffusion of second messengers is, by itself, a significant advance in the field. With appropriate modifications (such modifications will be known to those of ordinary skill in the art upon consideration of the present disclosure), a model of the present invention can be extended to understand and describe, for example, light and dark adaptation in rods, and a similar analysis is possible for the study of vertebrate cones, which mediate color vision. The transduction mechanism of vertebrate cones is very much like that of the rods (Stryer, (1991) *J. Biol. Chem.* 266: 10711–10714). By employing the present invention, the coupling of cones and rods can be explored, for example by a homogenization limit of their periodic distribution along the retina. When implemented computationally, the generation of a "virtual" retina to aid in the diagnosis of retinal degeneration and other visual defects, for example, is possible.

The mechanisms of signal transduction described herein are fundamentally similar to signal transduction mechanisms employed by G-protein-coupled receptors. For example, G-protein-mediated signal transduction forms an element of vertebrate senses, such as olfaction and taste, hormonal signal transduction, chemotaxis and neurotransmitter signal transduction in the brain (Stryer, (1991) *J. Biol.*

Chem. 266: 10711–10714). Successful mechanism-based mathematical modeling of even a single sophisticated signal transduction feedback system, coupled with the implementation of a computer simulation that is accessible to researchers, can provide guidance for additional models. For example, the guidance provided by a vision transduction model can be employed in a model of other signal transduction pathways that interact and/or overlap in vivo.

Indeed, by employing a model of the present invention as a starting point, it is possible to build up individual "signaling modules". Such modules can be of assistance to researchers working on problems associated with understand the networks of signal transduction pathways that underlie complex cellular responses to signals. These mathematical models, which can be implemented on one or more computers, can be useful for modeling the pathology underlying diseases that implicate signaling pathways, such as cancer. Quantitative models, such as those of the present invention, can also be employed in drug discovery efforts. In this capacity, these models can help identify target proteins that are positioned at a site in a signal transduction network such that inhibition of these proteins might give rise to therapeutic effects.

Those of ordinary skill in the art will appreciate that, upon consideration of the present disclosure, the models and methods of the present invention can be modified beyond the particular embodiments disclosed herein. For example, in other embodiments, similar homogenization methods can be applied to complex geometries disposed in other cell types. In this capacity, the methods can allow researchers to precisely model the particular spatial locations of the elements of a signaling pathway within a cell, as well as the spatial and temporal evolution of the pathway. This is a dramatic improvement over the current models that are based upon ordinary differential equations (Weng et al., (1999) *Science* 284: 92–96 and Bhalla et al., (1999) *Science* 283: 381–387). Broadly, the methods of the present invention can be employed to any biological process in which localized reactions are taking place, including those in which some reactants are disposed on a surface (e.g., a membrane) while others are disposed in a volume (e.g., cytosol).

In another embodiment, the simulations of single signal transduction modules can be built up and interfaced with one another to model signal transduction pathways interacting in ways known from biological experimentation, or predicted based on evaluation of a model. Thus, the methods and models of the present invention, which can be embodied in a computer readable medium, can be used to build up a model of a signal transduction network to test specific hypotheses of signal cross-talk, integration and decision-making.

REFERENCES

The references listed below as well as all references cited herein are incorporated by reference to the extent that they supplement, explain, provide a background for or teach methodology, techniques and/or compositions employed herein. All cited patents and publications referred to in this application are herein expressly incorporated by reference.

Adams, *Sobolev Spaces*, Academic Press, New York, 1975
Alexiades et al., (1996) *Commun. Numer. Meth. En.* 12: 31–42
Baiocchi, (1993) in *Boundary Value Problems for Partial Differential Equations and Applications* (Baiocchi, Lions, eds.), Research Notes in Applied Mathematics 29, Masson, Paris, pp. 293–297 (1993)
Baylor et al., (1979) *J. Physiol.* 288: 613–634
Baylor, (1996) *Proc. Nat. Acad. Sci. USA* 93: 560–565
Bensoussan et al., *Asymptotic Analysis for Periodic Structures*, North-Holland Publishing, Amsterdam, Holland (1978)
Bhalla et al., (1999) *Science* 283: 381–387
Bownds et al., (1995) *Behavioral Brain Sci.* 18: 415–424
Burns et al., (2001) *Ann. Rev. Neurosci.* 24: 779–805
Chen et al., (1995) *Science* 267: 374–377
Chen et al., (1999) *Proc. Natl. Acad. Sci. USA* 96: 3718–3722
Chen et al., (2000) *Nature* 403: 557–560
Ciarlet & Lods, (1996) *Arch. Rational Mech. Anal.* 136: 119–161
Cioranescu & Paulin, *Homogenization of Reticulated Structures*, Springer-Verlag, New-York, 1999, *Applied Mathematical Sciences* Vol. 136
Colli & Rodrigues, (1990) *Asymptotic Anal.* 3: 249–263;
Dauge & Gruais, (1996) *Asymtotic Anal.* 13: 167–197
Detwiler et al., (1996) *Curr. Opin Neurobiol.* 6(4): 440–444
Detwiler et al., (2000) *Biophys. J.* 79(6): 2801–2817
DiBenedetto, *Real Analysis*, Birkhäuser, Boston, 2000
Dumke et al., (1994) *J. Gen. Physiol.* 103: 1071–1098
Erzhanov et al., *Concentrated Capacity in Problems of Thermophysics and Micro-Electronics*, Naukova Dumka, Kiev, 1992
Gray-Keller et al., (1999) *J. Physiol.* 519: 679–692
Hamm, (1991) in *Cellular and Molecular Neurobiology*, (Saavedra, ed.) 11: 563–578
Hargrave et al., *FASEB J.* 6(6): 2323–2331
Hurley, (1994) *Curr. Opin. Neurobiol.* 4: 481–487
Jäger et al., (1997) *Appl. Anal.* 65: 205–223
Koutalos & Nakatani, (1999) *Biophys.J.* 76: A242
Koutalos & Yau, (1996) *Trends Neurosci.* 19: 73–81
Koutalos et al., (1995) *Biophys. J.* 68: 373–382
Lagnado et al., (1992) *J. Physiol.* 455: 111–142
Lamb et al., (1981) *J. Physiol.* 319: 463–496
Lamb, (1980) *Nature* 287: 349–351
Leskov et al., (2000) *Neuron* 27:525–537
Liebman et al., (1987) *Ann. Rev. Physiol.* 49: 765–791
Magenes, (1991) in *Nonlinear Analysis, a tribute in honour of Giovanni Prodi*, (Ambrosetti & Marino, eds.), Scuola Normale Superiore, Pisa, pp.217–229
Magenes, (1998) *Boll. Un. Mat. Italiana,* 1B, N.8, pp.71–81
Matthews et al., (1988) *Nature* 334: 67–69
Mazja, *Sobolev Spaces*, Springer-Verlag, New York, 1985
Meirmanov, (1972) *Dinamika Splosn. Sredy* 10: 85–101
Motygin & Nazarov, (2000) *IMA J. Appl. Math.* 65:1–28
Nakatani & Yau, (1988) *J. Physiol.* 395: 695–729
Nikonov et al., (2000) *J. Gen. Physiol.* 116: 795–824
Noel et al., (1993) *Nature* 366: 654–663
Oleinik & Shaposhnikova, (1995) *Rendiconti Lincei: Matematica e Applicazioni* 6: 133–142
Oleinik et al., *Mathematical Problems in Elasticity and Homogenization*, North Holland Publishing, Amsterdam, Holland 1992
Palczewski et al., (2000) *Science* 289: 739–745
Pawson et al., (1997) *Science* 278: 2075–80
Pugh & Lamb, (1993) *Biochim. Biophys. Acta* 1141: 111–149
Pugh et al., *Curr. Opin Neurobiol.* 9: 410–480
Rieke & Baylor, (1998) *Biophysical J.* 75: 1836–1857
Rychter, (1988) *Int. J. Solids Struct.* 24: 537–544
Savarè & Visintin, (1997) *Atti delta Accademia nazionale dei Lincei. Classe di scienze fisiche, matematiche e naturali. Rendiconti lincei. Matematica e applicazioni* 8(1): 49–89
Weng et al., (1999) *Science* 284: 92–96
Yosifian, (1997) *Appl. Anal.* 65: 257–288

It will be understood that various details of the invention may be changed without departing from the scope of the invention. Furthermore, the foregoing description is for the purpose of illustration only, and not for the purpose of limitation.

What is claimed is:

1. A method of modeling a signal transduction pathway in a cell, the method comprising:
   (a) determining a simulated geometry of a signaling pathway in a cell; and
   (b) calculating spatial and temporal diffusion of a chemical species via the simulated geometry of the signal transduction pathway in the cell, whereby signal transduction in the cell is modeled.

2. The method of claim 1, wherein the cell is a vertebrate cell.

3. The method of claim 2, wherein the vertebrate cell is selected from the group consisting of a rod cell of an eye, a cone cell of an eye and a tumor cell.

4. The method of claim 1, wherein the simulated geometry is determined by employing one of homogenization theory and a concentrated capacity, and combinations thereof.

5. The method of claim 1, wherein the spatial and temporal diffusion of a chemical species comprises a coupled diffusion.

6. The method of claim 1, wherein the calculating comprises employing partial differential equations to describe the diffusion of the chemical species.

7. The method of claim 1, further comprising modeling signal transduction in a plurality of cells, whereby modeling of signal transduction in a tissue is accomplished.

8. A program storage device readable by a machine, tangibly embodying a virtual cell model produced by the method of any of claims 1–6.

9. A program storage device readable by a machine, tangibly embodying a virtual tissue model produced by the method of claim 7.

10. The program storage device of claim 9, wherein the virtual tissue model is an eye model.

11. A program storage device readable by a machine, tangibly embodying a program of instructions executable by the machine to perform method steps for modeling a signal transduction pathway in a cell, the steps comprising:
   (a) determining a simulated geometry of a signaling pathway in a cell; and
   (b) calculating spatial and temporal diffusion of a chemical species via the simulated geometry of the signal transduction pathway in the cell, whereby a signal transduction pathway in the cell is modeled.

12. The program storage device of claim 11, wherein the cell is a cell of a vertebrate.

13. The program storage device of claim 12, wherein the cell is a rod cell of a vertebrate eye.

14. The program storage device of claim 11, wherein the simulated geometry is determined via homogenization theory, concentrated capacity, or combination thereof.

15. The program storage device of claim 11, wherein the spatial and temporal diffusion of a chemical species comprises a coupled diffusion.

16. The program storage device of claim 11, further comprising the step of modeling signal transduction in a plurality of cells, whereby modeling of signal transduction in a tissue is accomplished.

17. A method of modeling the diffusion of two or more entities in a medium, the method comprising:
   (a) mathematically describing a medium;
   (b) determining boundary source terms for two or more entities;
   (c) expressing the diffusion of at least one of the two or more entities as a homogenized limit;
   (d) expressing the diffusion of at least one of the two or more entities as a concentrated capacity limit; and
   (e) calculating a spatial and temporal diffusion of one or more of the two or more entities by evaluating the homogenization limit and the surface evolution equation, whereby the diffusion of two or more entities in a medium is modeled.

18. The method of claim 17, wherein the medium is a cell.

19. The method of claim 18, wherein the medium is a rod outer segment.

20. The method of claim 17, wherein the expressing and the concentrating are by employing partial differential equations.

21. The method of claim 17, wherein the two or more entities are selected from the group consisting of cGMP, cGMP phosphodiesterase, activated cGMP phosphodiesterase, $Ca^{2+}$, rhodopsin, activated rhodopsin, transducin and activated transducin.

22. The method of claim 17, wherein the boundary source terms are determined are determined for a species selected from the group consisting of $Ca^{2+}$ and cGMP.

23. The method of claim 17, wherein the diffusion process is concentrated on the outer surface of a rod cell.

24. A program storage device readable by a machine, tangibly embodying a program of instructions executable by the machine to perform the method steps of any of claims 17–23.

25. A program storage device readable by a machine, tangibly embodying a program of instructions executable by the machine to perform method steps for modeling diffusion of two or more entities in a medium, the steps comprising:
   (a) mathematically describing a medium;
   (b) determining boundary source terms for two or more entities;
   (c) expressing the diffusion of at least one of the two or more entities as a homogenized limit;
   (d) expressing the diffusion of at least one of the two or more entities as a concentrated capacity limit; and
   (e) calculating a spatial and temporal diffusion of one or more of the two or more entities by evaluating the homogenization limit and the surface evolution equation, whereby the diffusion of two or more entities in a medium is modeled.

26. The program storage device of claim 25, wherein the medium is a cell.

27. The program storage device of claim 26, wherein the medium is a rod outer segment.

28. The program storage device of claim 25, wherein the expressing and the concentrating are by employing partial differential equations.

29. The program storage device of claim 25, wherein the two or more entities are selected from the group consisting of cGMP, cGMP phosphodiesterase, activated cGMP phosphodiesterase, $Ca^{2+}$, rhodopsin, activated rhodopsin, transducin and activated transducin.

30. The program storage device of claim 25, wherein the boundary source terms are determined are determined for a species selected from the group consisting of $Ca^{2+}$ and cGMP.

31. The program storage device of claim 25, wherein the diffusion process is concentrated on the outer surface of a rod cell.

* * * * *